(12) United States Patent
Mor et al.

(10) Patent No.: US 11,159,769 B2
(45) Date of Patent: Oct. 26, 2021

(54) DROWNING DETECTION ENHANCED BY SWIMMER ANALYTICS

(71) Applicant: Lynxight LTD, Haifa (IL)

(72) Inventors: Roee Mor, Haifa (IL); Omer Bar Ilan, Haifa (IL)

( * ) Notice: Subject to any disclaimer, the term of this patent is extended or adjusted under 35 U.S.C. 154(b) by 132 days.

(21) Appl. No.: 16/056,527

(22) Filed: Aug. 7, 2018

(65) Prior Publication Data

US 2020/0053320 A1 Feb. 13, 2020

(51) Int. Cl.
| | | |
|---|---|---|
| G08B 21/08 | (2006.01) | |
| G06K 9/00 | (2006.01) | |
| H04N 7/18 | (2006.01) | |
| G16H 10/60 | (2018.01) | |
| G16H 50/30 | (2018.01) | |

(52) U.S. Cl.
CPC ........... H04N 7/18 (2013.01); G06K 9/00335 (2013.01); G08B 21/08 (2013.01); G16H 10/60 (2018.01); G16H 50/30 (2018.01)

(58) Field of Classification Search
CPC .......... H04N 7/18; G16H 50/30; G16H 10/60; G06K 9/00335; G08B 21/08
USPC ........................................................ 348/157
See application file for complete search history.

(56) References Cited

U.S. PATENT DOCUMENTS

| | | | | |
|---|---|---|---|---|
| 2016/0005292 A1* | 1/2016 | Carroll | ................... | G08B 21/08 340/539.13 |
| 2016/0104359 A1* | 4/2016 | AlMahmoud | ........... | G01S 15/42 367/112 |
| 2016/0340006 A1* | 11/2016 | Tang | ..................... | B64C 39/024 |
| 2018/0040223 A1* | 2/2018 | Bodi | .................... | G08B 21/086 |
| 2019/0034712 A1* | 1/2019 | Golan | ................... | G06T 7/0002 |

FOREIGN PATENT DOCUMENTS

| | | |
|---|---|---|
| CN | 101719216 A | 6/2010 |
| CN | 103413114 A | 11/2013 |
| WO | 2017130187 A1 | 8/2017 |

OTHER PUBLICATIONS

International Search Report with Written Opinion issued for corresponding International Application No. PCT/IL2019/050730 dated Oct. 10, 2019.

* cited by examiner

*Primary Examiner* — John W Miller
*Assistant Examiner* — Omer Khalid

(57) ABSTRACT

A system, a computerized apparatus and a method for drowning detection based on swimmer analytics. The method comprises obtaining a visual input cameras observing a water area and analyzing each swimmer in the water area based on the visual input. Said analyzing comprises determining a risk level of each swimmer, whereby a first risk level is determined for a first swimmer and a second risk level is determined for a second swimmer, wherein the first risk level is higher than the second risk level; and automatically detecting potential drowning events for each swimmer. Said automatically detecting is performed by utilizing computational resources in a non-uniform manner. Said automatically detecting comprises applying increased computational resources with respect to the first swimmer, and applying reduced computational resources with respect to the second swimmer. The increased computational resources are higher than the reduced computational resources.

23 Claims, 8 Drawing Sheets

DROWNING DETECTION ENHANCED BY SWIMMER ANALYTICS

TECHNICAL FIELD

The present disclosure relates to computer vision for drowning detection in general, and to drowning detection enhanced by swimmer analytics, in particular.

BACKGROUND

Modern pools or water areas that are designated for swimming may be monitored with safety camera that provide data for lifeguards or monitoring systems. Pool safety cameras may be video monitoring or recording systems designed to improve safety, such as by reducing drowning injuries or deaths in public and private pools.

Aquatics monitoring systems may be either passive systems or active systems. Passive systems provide lifeguards with views of above or below water swimmer activity and behavior. The views help the lifeguards themselves to identify an incident developing or abnormal events occurring. They may be primarily a means of addressing the physical limitations of viewing through glare and into blind spots in the water area. Active systems may be designed to further help lifeguards in an attempt to address the physical limitations imposed by the human factor. Additionally or alternatively, active systems may be configured to detect safety events automatically and generate an alert to the lifeguard or other relevant personnel.

BRIEF SUMMARY

One exemplary embodiment of the disclosed subject matter is a method for drowning detection based on swimmer analytics. The method may comprise: obtaining a visual input from one or more cameras observing a water area; analyzing each swimmer in the water area, based on visual input from the one or more cameras, wherein said analyzing may comprise determining a risk level of each swimmer, whereby a first risk level may be determined for a first swimmer and a second risk level may be determined for a second swimmer, wherein the first risk level may be higher than the second risk level; and automatically detecting potential drowning events, for each swimmer, wherein said automatically detecting may be performed by utilizing computational resources in a non-uniform manner, wherein said automatically detecting may comprise applying increased computational resources with respect to the first swimmer, and applying reduced computational resources with respect to the second swimmer, wherein the increased computational resources may be higher than the reduced computational resources.

Optionally, the risk level of each swimmer may be related to drowning potential of the each swimmer.

Optionally, the analysis may comprise determining a descriptor for each swimmer, wherein the a descriptor may comprise at least one of the following: demographic information, an estimated swimming quality level, a behaviour descriptor of the each swimmer in the water area, and an interaction descriptor of the each swimmer with other swimmers in the water area; and the risk level of each swimmer may be determined based on the descriptor of the each swimmer.

Optionally, the analysis may comprise extracting descriptor about the each swimmer from a database, wherein the descriptor may comprise at least one of the following: medical information and depiction of normal swimming activity; and wherein the risk level of each swimmer may be determined based on the descriptor of the each swimmer.

Optionally, determining the risk level of the each swimmer may comprise determining a location of the each swimmer, retrieving a risk level of the location of the each swimmer, wherein the risk level of the each swimmer may be based on the risk level of the location of the each swimmer.

Optionally, the method may comprise having a first classifier and a second classifier, both configured to predict a likelihood of a potential drowning event, wherein the first classifier may be configured to utilize the increased computational resources, wherein the second classifier may be configured to utilize the reduced computational resources, wherein said automatically detecting may comprise applying the first classifier with respect to the first swimmer, and applying the second classifier with respect to the second swimmer.

Optionally, the first classifier may be configured to receive a first set of features, wherein the second classifier may be configured to receive a second set of features, wherein a Cartesian product of domains of the first set of features may comprise a larger number of elements than a Cartesian product of domains of the second set of features.

Optionally, the first classifier may be configured to receive a first set of features, wherein the second classifier may be configured to receive a second set of features, wherein the first set of features may comprise a first feature, wherein the second set of features may comprise a second feature, wherein the first feature and the second feature may be representative of a same trait, wherein a number of potential values of the first feature may be greater than a number of potential values of the second feature.

Optionally, automatically detecting may comprise applying a detection algorithm for the first and second swimmers periodically, wherein said applying may comprise applying the detection algorithm at a first rate for the first swimmer and applying the detection algorithm at a second rate for the second swimmer, wherein the first rate may be higher than the second rate.

Optionally, automatically detecting may comprise: obtaining a first visual input with respect to the first swimmer; obtaining a second visual input with respect to the second swimmer, wherein the first visual input may comprise more information than the second visual input; utilizing the first visual input in order to determine a potential drowning event with respect to the first swimmer; and utilizing the second visual input in order to determine a potential drowning event with respect to the second swimmer.

Optionally, the first and second visual inputs differ in at least one of the following: a resolution of images, a video frame rate, a patch size.

Optionally, said obtaining and said automatically detecting are performed periodically, wherein a rate at which said automatically detecting may be performed with respect to the first swimmer may be higher than a rate at which said automatically detecting may be performed with respect to the second swimmer.

Optionally, said analyzing may comprise identifying a spotter observing the second swimmer, wherein said determining the risk level of the second swimmer may be based on the spotter observing the second swimmer.

Optionally, the spotter may be one of the following: a personal spotter of the second swimmer; and a lifeguard in charge of the water area.

Optionally, said analyzing may comprise identifying a spotter, determining a field of view of the spotter, and wherein said determining the risk level may be performed based on the field of view of the spotter.

Optionally, the water area may comprise a first water area and a second water area, wherein the first and the second water areas are separated, wherein the first swimmer may be located in the first water area and the second swimmer may be located in the second water area.

Optionally, in response to said automatically detecting a potential drowning event: determining a location of a swimmer associated with the potential drowning event; and mechanically adjusting a position of a visual indicator configured to visually illuminate an area within the water area, wherein said mechanically adjusting may comprise adjusting the position so that the visual indicator may visually illuminate the location of the swimmer.

Optionally, said mechanically adjusting may comprise: adjusting the visual indicator to a first position; obtaining a second visual input from the one or more cameras; determining a visually illuminated area within the water area, wherein the visually illuminated area may be illuminated by the visual indicator; determining that the visually illuminated area may be different than the location of the swimmer; and mechanically re-adjusting the visual indicator to a second position, wherein in the second position the visual indicator visually may illuminate the location of the swimmer.

Optionally, said utilizing computational resources in a non-uniform manner may comprise applying a first algorithm to detect a potential drowning event of the first swimmer and applying a second algorithm to detect a potential drowning event of the second swimmer, wherein the second algorithm may be configured to utilize less computational resources than the first algorithm.

Optionally, the first algorithm may have a reduced likelihood of having a false negative detection of potential drowning events in comparison to the second algorithm.

Optionally, said automatically detecting may comprise comparing a confidence measurement of a detection algorithm with a respective threshold in order to determine existence of a potential drowning event; wherein said utilizing computational resources in a non-uniform manner may comprise setting a first threshold with respect to the first swimmer and a second threshold with respect to the second swimmer, wherein the first threshold may be lower than the second threshold, whereby a same detected potential event having a confidence measurement between the first threshold and the second threshold may be configured to be reported with respect to the first swimmer but not with respect to the second swimmer, whereby computational resources utilized with relation to the first swimmer are increased with respect computation resources utilized with relation to the second swimmer.

Another exemplary embodiment of the disclosed subject matter may be a system for drowning detection based on swimmer analytics, the system comprising: a one or more cameras observing a water area; a memory, wherein said memory retaining a plurality of alternative computer program products implementing drowning detection, wherein said memory retaining a mapping between swimmer descriptors and the plurality of alternative computer program products; a processor that may be configured to: analyze each swimmer in the water area, based on visual input from the one or more cameras, to determine a descriptor of the each swimmer; for each swimmer, select a computer program product from the plurality of alternative computer program products based on the descriptor of the each swimmer and the mapping; invoke, for each swimmer, the computer program product selected for the each swimmer; whereby the system may be tuned to utilize different drowning detection for different swimmers, whereby performance of the system may be enhanced with respect to utilization of uniform drowning detection for all swimmers.

Optionally, the plurality of alternative computer program products are a single configurable computer program product having a plurality of alternative configurations, wherein the selection of the computer program product may comprise selecting a configuration from the plurality of alternative configurations.

Optionally, the descriptor may comprise a relative location of the swimmer in relation to a marker in the water area, wherein the selection of computer program product may comprise selecting a drowning detection suited for swimmers located at the relative location.

Optionally, the processor may be further configured to determine for each swimmer, a water descriptor representing properties of a portion of the water area in which the swimmer may be located, wherein for at least two swimmers, there are two different water descriptors, wherein the selection of the computer program product may be further based on the water descriptor determined for the swimmer.

Optionally, the swimmer descriptor may be determined based on interaction between the swimmer and a one or more other swimmers, wherein the selection of the computer program product may be further based on the interaction between the swimmer and the one or more other swimmers.

Optionally, the plurality of alternative computer program products comprise a first classifier and second classifier, wherein the first and second classifiers are implementing a same classification algorithm, wherein the first classifier may be trained with respect to a first training dataset comprising information about swimmers having a first shared property, wherein the second classifier may be trained with respect to a second training dataset comprising information about swimmers having a second shared property, wherein the system may be configured to select the first classifier based on the descriptor having the first shared property, and wherein the system may be configured to select the second classifier based on the descriptor having the second shared property.

Optionally, the system further comprising: an alert module responsive to a drowning event of a swimmer of interest, identified by one of the plurality of alternative program products; wherein said alert module having a configurable alert threshold; wherein said processor may be configured to set the configurable alert threshold based on the descriptor of the swimmer of interest.

Optionally, said system may be configured to repeatedly re-compute the descriptor for the each swimmer, wherein re-computation rate may be determined based on a previously computed descriptor.

Yet another exemplary embodiment of the disclosed subject matter may be a computerized apparatus having a processor, the processor being adapted to perform the steps of: obtaining a visual input from one or more cameras observing a water area; analyzing each swimmer in the water area based on the visual input from the one or more cameras, wherein said analyzing may comprise determining a risk level of each swimmer, whereby a first risk level may be determined for a first swimmer and a second risk level may be determined for a second swimmer, wherein the first risk level may be higher than the second risk level; and automatically detecting potential drowning events, for each swimmer, wherein said automatically detecting may be performed by utilizing computational resources in a non-uniform manner, wherein said automatically detecting may comprise applying increased computational resources with respect to the first swimmer, and applying reduced computational resources with respect to the second swimmer, wherein the increased computational resources are higher than the reduced computational resources.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1A:
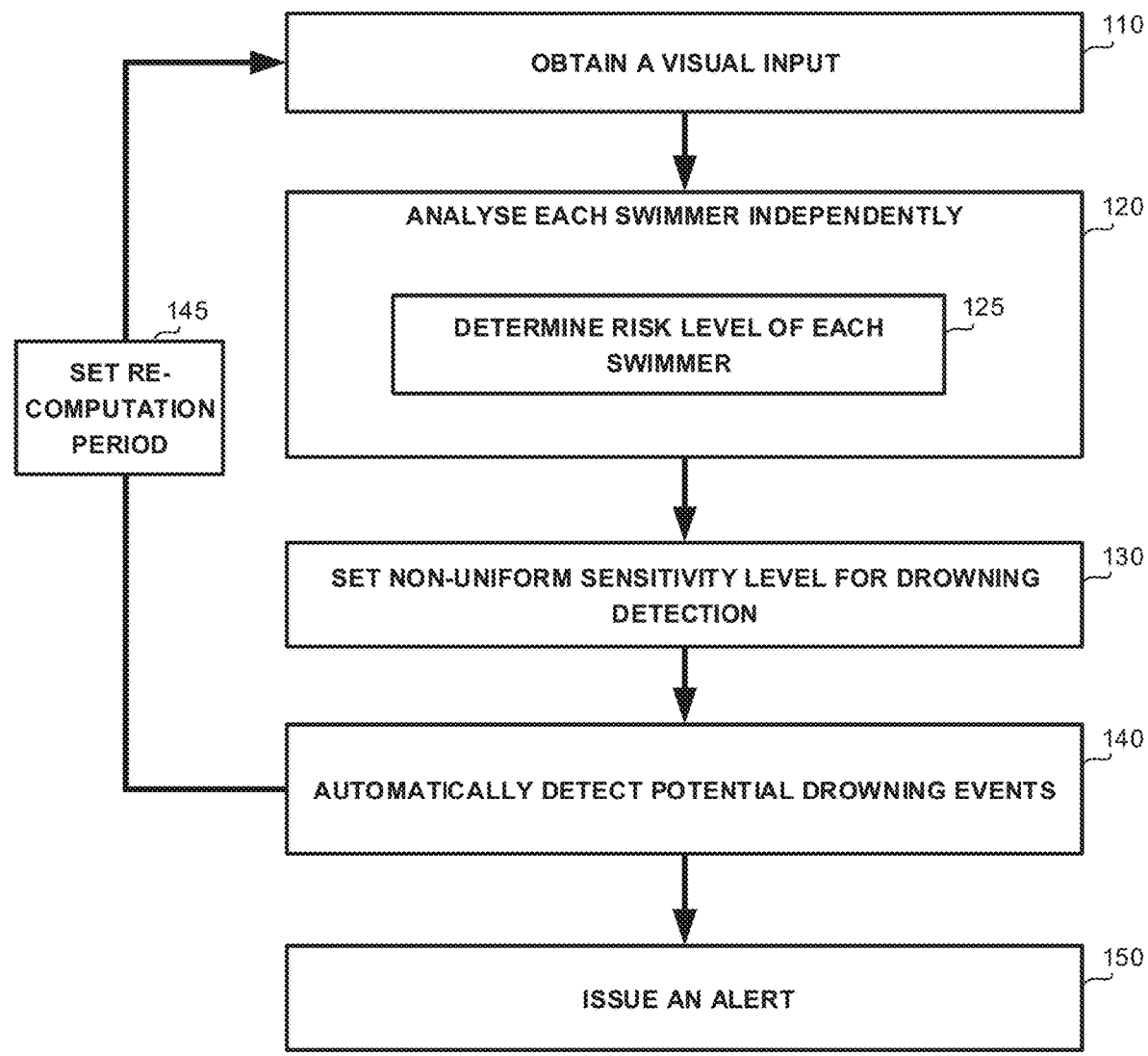
FIGS. 1A-1C show flowchart diagrams of a method, in accordance with some exemplary embodiments of the disclosed subject matter.

One technical problem dealt with by the disclosed subject matter is to improve the performance of drowning detection systems. Existing drowning detection systems, watch the whole water area of their response, uniformly. Locations or swimmers associated with risk may be inefficiently observed like other locations or swimmers, while utilizing the same amount of computational resources, the same algorithms, the same thresholds, or the like. As a result, such systems may be wasting their computational resources on events that may be not likely to be associated with risk.

Another technical problem dealt with by the disclosed subject matter is to enable an early detection of potential drowning events, potentially before an actual drowning is happening. In some exemplary embodiments, some computer-aided drowning detection systems, may detect actual drowning only after the drowning is already in an advanced state, i.e., when a person is lying motionless at the bottom of the pool. Some systems may be configured to feed a video from cameras into a computerized monitoring software package capable of tracking the activity of swimmers and alerting staff if swimmers exhibit known behaviors associated with the advanced stages of drowning—being submerged and static for an extended period of time.

As yet another technical problem dealt with by the disclosed subject matter is to enable the detection of drowning events that may be missed by existing downing detection systems. In some exemplary embodiments, pool safety systems may comprise three levels of safety protection: potential distress detection, distress detection and drowning detection. A drowning incident in the pool may start in the first level, e.g., when a swimmer is in a potential distress; and may progress to the next levels unless treated and stopped. Existing system may be only able to handle the third level, e.g., when the swimmer is already drowning. Catching incidents in the first two levels may enable to completely avoid the risks and implications of actual drowning. An early detection of low severity events before the swimmer starts drowning may be needed.

Additionally or alternatively, some drowning incident may start in the final level, e.g., a direct occurrence of a drowning event without developing through the lower events. Such incidents may be required to be detected and treated immediately. In some cases an early detection, may not even be possible.

One technical solution is to reallocate, in real time, computational resources of drowning detection system, based on swimmers' analytics. Swimmers or locations within the pool that may be determined to be in a higher risk level, may be provided with higher computational resources in order to enable earlier detection of potential drowning events. In some exemplary embodiments, the computational resources of the drowning detection system, may comprise for example, the amount of features utilized to classify the events, details of such features, resolution of the visual input, patch size of the visual input, frame rate at which visual input is observed, or the like. Additionally or alternatively, the computational resources of the drowning detection system, may comprise a type of the algorithms utilized for the classification, complexity of such algorithms, the computational resources utilized by such algorithms, or the like. Additionally or alternatively, the computational resources may comprise thresholds at which a classification is determined.

In some exemplary embodiments, a visual input may be obtained from one or more cameras observing a water area, such as a pool. Different swimmers may be detected in the water area. In some exemplary embodiments, artificial intelligence algorithms may be applied in order to learn the water area scene as a human observer sees. Early tell-tale signs of drowning may be searched in the visual input.

In some exemplary embodiments, each swimmer in the water area may be analyzed independently from other swimmers. Additionally or alternatively, interaction between each swimmer and the other swimmers in the water area may be analyzed. Swimmers and interaction therebetween in the water area may be analyzed using computer vision and machine learning. Each situation of each swimmer may be classified as safe, being in a potential distress, being in actual distress, or the like. As an example, children in the water with no adults around them, or without a floatation device may be considered to be in a potential distress situations. As another example, a swimmer lying face down in the water, or significant slowing down in swimming pace after swimming fast, may be considered to be in a distress situations. As another example, swimmers involved in a fight in the water area, or aggressively playing with other swimmers, may be considered to be in a distress situation.

In some exemplary embodiments, the classification of the swimmers may be performed based on the analysis of the water area, the swimmers, or the like. The analysis may comprise determining a descriptor for each swimmer. The descriptor may comprise demographic information (e.g., gender, age, or the like), an estimated swimming quality level (e.g., athletic swimmer, beginner, or the like), special gestures (e.g., waving hands), special motion (e.g., continuously diving, lying with the face down, jumping, or the like), use of floatation or buoyancy devices, or the like.

In some exemplary embodiments, a risk level of each swimmer may be determined. The risk level may be an attribute of the swimmer in the pool. In some exemplary embodiments, the risk level may be a scalar value, a real value, or the like. Additionally or alternatively, the risk level may be a record comprising a plurality of fields, each of which associated with a different potential risk factor. For example, the risk level may comprise an "underwater risk factor" and a "swimming ability risk factor". The risk level may be determined based on information gathered and processed by the system related to that swimmer. The risk level may be determined based on the descriptor of the swimmer, such as age, size, gender, or the like. Additionally or alternatively, the risk level may be determined based on behaviors of the swimmer, such as swimming ability, location in the pool (shallow or deep water), visibility by the spotters, aggressive behavior, or the like. It may be noted that the risk level can change over time.

In some exemplary embodiments, the descriptor of the swimmers may be collected by the system based on the visual input received from the cameras observing the water areas. The system may be configured to determine the descriptor based on the visual appearance of the swimmers, based on measurements of the swimmers, or the like. As an example, swimmers shorter than 1.20 meters may be determined to be children. The age of the children may be determined with respect to the length. As another example, a swimming level of the swimmer may be determined based on the swimming pace, the number or rate of extended diving events the swimmer performed, or the like. In some exemplary embodiments, the system may be configured to determine the risk level of each swimmer based on the descriptor and behavior determined based on the visual input.

Additionally or alternatively, such information may be provided externally from the system. In some exemplary embodiments, a database retaining identifiers of swimmers may be maintained. The database may be associated with the water area, and may be configured to retain information of swimmers that usually bathe in the water area, information about each swimmer that ever entered the water area, identifiers thereof, swimming level of each swimmer, or the like. As an example, in some clubs, membership information may be retained. Each member of the club may provide, for example upon registration, a photo, medical information, demographic information, or the like. The photo may be retained in the database along with other information of the member. The member may be identified when swimming in the water area, based on her photo, and information related thereto may be extracted from the database. Additionally or alternatively, each swimmer may be distinctively identified, such as based on the descriptor of the swimmer, the demographic information of the swimmer, the physiological information of the swimmer, or the like. Each swimmer identified in the visual input may be searched for in the database, and specific information about the swimmer may be extracted therefrom. The specific information may be utilized to determine the risk level of the swimmer. As an example, swimmers suffering from heart or neurological problems may be determined to be in a higher risk level and should be more closely and sensitively monitored than healthy individuals. As another example, a swimmer may be configured as a "never diving" swimmer, so that if the swimmer is observed underwater for even a brief period, the system may understand that it is an abnormal situation. As yet another example, the system may be configured to automatically learn each swimmer's individual swimming patterns (such as time of day, distance, duration, swimming style, skill level, or the like), and retain it in the database. In response to identifying the swimmer is swimming outside the regular pattern, the swimmer may be determined to be in a higher risk level and the system may be configured to pay closer attention to the swimmer Additionally or alternatively, a risk level of each portion of the water area may be determined. Dangerous areas, such as deep water, highly crowded area, or the like, may be determined to be areas with a higher risk level and higher likelihood of containing distress situations. Such areas may be required to be observed and watched more closely for all swimmers or for swimmers of a certain type (e.g., deep water may be considered at a higher risk level for children under age 12 but not for adults above age 18). As an example, an area which is hard to be observed by the lifeguard at a certain time period due to glare from the sun, due to some object blocking the lifeguard's view, or the like, may be determined to be in a higher risk level, and more resources of the system may be appropriated there. As another example, an area that is close to a diving board or a water slide where people jump in the pool may be determined to be in a higher risk level for due to people jumping or falling into the water and resurfacing. It is also noted that in such areas, people diving in water and resurfacing may occur frequently and the normal activity pattern of swimmers in such areas may be different than their normal activity pattern in other portions of the water area.

It may be appreciated that the risk kevel may be time dependent, and may be continuously determined, such as re-determined every 10 minute, every 5, minutes, or the like.

In some exemplary embodiments, an event severity may be determined for each even recognized by the system. The event severity may be classified based on a swimmer not being in distress at all (e.g., safe situation), a swimmer being in a potential distress, a swimmer being in actual distress, or a swimmer already drowning. As an example, a person running around the pool may be determined to be in a potential distress, and accordingly may be associated with a high event severity. As another example, a swimmer performing an erratic limb movement may be in an actual distress and accordingly may be associated with a higher severity.

In some exemplary embodiments, potential drowning events may be automatically detected for each swimmer using machine learning. Potential drowning events may be events with high severity that the system classifies as potential drowning. It may be appreciated that not all detected events may warrant an immediate alert to the emergency personnel (e.g. lifeguard, security guard, or the like). Some of the swimmer's behaviors or attributes may cause the system to increase its sensitivity and give more focus to the swimmer, in order to carefully monitor if the swimmer is developing actual distress. As an example, the system response in case of unsafe behavior may be increasing the systems sensitivity for the relevant swimmer, and handling the event according to its risk. The system response in case of an actual distress may be further increasing the systems sensitivity for the relevant swimmer, and alerting to an emergency personal, while the system response in case of an actual drowning may be issuing an urgent alert.

In some exemplary embodiments, the system sensitivity may be tuned by utilizing computational resources of the system in a non-uniform manner. Increased computational resources may be applied in areas with swimmers with higher risk levels, areas in the pool with higher risk levels, or the like. The system sensitivity may be a gauge for controlling the distribution of computational resources around the water area. The system may be configured to allocate additional computational resources to areas with a distress or potential drowning event, e.g., events with a higher severity. Such additional resources may come at the expense of the remaining areas which have less resources allocated to them.

In some exemplary embodiments, the computational resources that may be applied in a non-uniform manner may be related to the quality of the visual input, such as image resolution, video frame rate, patch size, accuracy, which camera the visual input is being obtained from, utilizing visual input from a single camera or a group of cameras, or the like. Additionally or alternatively, the computational resources may be related to the quality of analysis of the visual input, the quality of classification of events, or the like; such as the amount of features utilized in the classification, quality and detail of these features, or the like. Additionally or alternatively, the computational resources may be related to the rate at which descriptors and information is updated. As an example, in case of a low risk level, the rate at which the swimmer is inspected may be reduced.

Another technical solution is to change, in real time, parameters of drowning detection system, based on swimmers' analytics, such as changing thresholds at which events are alerted, algorithms that are used to determine event severity, or the like.

In some exemplary embodiments, swimmers or locations within the pool that are determined to be in a higher risk level, may be re-associated with lower thresholds at which the events are alerted, to enable an earlier intervention of the rescue personal, and prevention of potential drowning events. In some exemplary embodiments, the automatic detection of the drowning events may comprise comparing a confidence measurement of a detection algorithm with a respective threshold in order to determine existence of a potential drowning event. Thresholds that are applied with respect to swimmers that are associated with lower risk levels may be configured to be lower than thresholds that are applied with respect to swimmers that are associated with higher risk levels.

Additionally or alternatively, different algorithms, such as algorithms with different complexity, different parameters, different accuracy level, or the like, may be utilized for swimmers or locations with higher risk level. In some exemplary embodiments, the automatic detection of drowning events may comprise applying a detection algorithm for the swimmers periodically. In some exemplary embodiments, the algorithms may be applied in different rates for swimmers associated with different risk levels. Additionally or alternatively, different algorithms may be applied for different swimmers that are associated with different risk levels. Algorithms that are applied with respect to swimmers that are associated with lower risk levels may be configured to utilize less computational resources than algorithms that are applied with respect to swimmers that are associated with higher risk levels.

Additionally or alternatively Algorithms that are applied with respect to swimmers that are associated with lower risk levels may have a reduced likelihood of having a false negative detection of potential drowning events in comparison to algorithms that are applied with respect to swimmers that are associated with higher risk levels.

In some exemplary embodiments, the risk level may be further determined based on a field view of a spotter observing the swimmer. The spotter may be a person that is tasked, formally or informally, with observing a swimmer, a group of swimmers, a water area, or the like, and preventing drowning events. The spotter may be a personal spotter of a certain swimmer, or group of swimmers, a lifeguard in charge of the water area, or the like. Being in a field of view of a spotter, may reduce the risk level of the swimmer.

In some exemplary embodiments, the detected event may be alerted to lifeguard(s), emergency personal or any other people in the water area. The event may be alerted using a visual pointer that points towards the detected events. The visual pointer may be mounted above the water area, in order to create a light beam directed at any point in the pool without risk of occlusion. The visual pointer may be configured to point towards the swimmer or the area associated with the event using different colors indicating different levels of alert. The visual pointer may be configured to direct the spotter exactly to the location of the event.

As yet, another technical solution is to tune drowning detection systems to utilize different drowning detection for different swimmers. The performance of the system may be enhanced with respect to utilization of uniform drowning detection for all swimmers. In some exemplary embodiments, a descriptor for each swimmer in the water area, may be determined, based on swimmers analysis.

In some exemplary embodiments, the system may be configured to retain a plurality of alternative computer program products implementing drowning detection and a mapping between swimmer descriptors and the plurality of alternative computer program products.

The system may be configured to select for each swimmer, a computer program product from the plurality of alternative computer program products based on the descriptor thereof, and in accordance with the mapping. The system may be configured to invoke the computer program product selected for each swimmer.

In some exemplary embodiments, the plurality of alternative computer program products may be a single configurable computer program product having a plurality of alternative configurations. The system may be configured to select for each user, a configuration for the single configurable computer program product, based on the descriptor thereof. The system may be configured to execute configurable computer program product with the configuration selected for the swimmer, in order to apply drowning detection for the swimmer.

In some exemplary embodiments, the descriptor may comprise a relative location of the swimmer in relation to a marker in the water area. The system may be configured to select computer program product suited for swimmers located at the relative location.

Additionally or alternatively, the system may be configured to determine for each swimmer, a water descriptor representing properties of a portion of the water area in which the swimmer is located, such as the depth of the water, a color of the background of the water area, or the like. Different swimmers may be assigned with different water descriptors. The selection of the computer program product may be further determined based on the water descriptor determined for the swimmer. Additionally or alternatively, the water descriptor may be comprised by the swimmer descriptor. As an example, the swimmer descriptor may indicate a proportion between the swimmer's height and the depth of the water, the swimmer's swimming level and the depth of the water, or the like.

Additionally or alternatively, the swimmer descriptor may be determined based on interaction between the swimmer and a one or more other swimmers, such as the swimmer being observed by the one or more other swimmers, the swimmer playing with one or more other swimmers, the swimmer being assimilated between the one or more other swimmers, or the like.

One technical effect of utilizing the disclosed subject matter is to detect potential distress and distress events before they become harmful. As indicated above, some drowning detection system may be only able to detect drowning events that are already happening. Catching incidents before an actual drowning is happening may enable to completely avoid the risks and implications of actual drowning. Furthermore, the disclosed subject matter enables to detect drowning events which occurred immediately without possibility of early detection.

Another technical effect of utilizing the disclosed subject matter is to provide for a better indication of drowning events. Existing systems have audible alarms, or monitors which show the location of distress on a diagram of the pool. The disclosed subject matter provides a direct indication for the drowning event that is directed not only to the emergency personal, but can also inform other swimmers or people in the water area of the event. Pointing directly to the area of distress in the water area, enables the emergency personal to see the alert without losing eye contact with the water or other swimmers for inspecting a monitor or other external device. Furthermore, the disclosed subject matter suggests to continue tracking and pointing towards the swimmer associated with the drowning event, so the emergency personal can be efficiently directed to the source of the distress.

As yet another technical effect of utilizing the disclosed subject matter is to enhance the performance of drowning detection systems. The disclosed subject matter enables to utilize the computational resources of drowning detection systems in a non-uniform matter, such that events with a higher severity are handled with more computational resources than events with a lower severity. The disclosed subject matter suggest to distribute the existing computational resources of such system, in a non-uniform manner, to provide more power and resources to events with real risk. The disclosed subject matter enables to efficiently use existing resources, instead of uniformly using such resources and wasting the resources on relatively safe swimmers or events.

The disclosed subject matter may provide for one or more technical improvements over any pre-existing technique and any technique that has previously become routine or conventional in the art. Additional technical problem, solution and effects may be apparent to a person of ordinary skill in the art in view of the present disclosure.

Referring now to FIG. 1A showing a flowchart diagram of a method, in accordance with some exemplary embodiments of the disclosed subject matter.

On Step 110, a visual input may be obtained. In some exemplary embodiments, the visual input may be a video, an image, a sequence of images, a combination thereof, or the like. In some exemplary embodiments, the visual input may be obtained from one or more cameras observing a water area. The one or more cameras may be located substantially above the water area being monitored. The one or more cameras may comprise an overhead camera that is positioned outside of the water. The water area being monitored may be referred to as a pool, but the disclosed subject matter may be employed in other scenarios, such as monitoring lakes, ponds, or other bodies of water in which people may bath.

In some exemplary embodiments, the water area may comprise more than one separated water area. Different swimmers may be bathing in each water area. The separated water area may be observed using different cameras, using a single camera, or the like. The visual input may descriptive of all of the separated water areas, a portion thereof, or the like.

In some exemplary embodiments, the visual input may comprise one or more swimmers bathing in the water.

On Step 120, each swimmer may be analyzed independently from the other swimmers, based on the visual input. In some exemplary embodiments, each swimmer may be tracked and analyzed independently from other swimmers. Additionally or alternatively, interaction of the each swimmer with other swimmers may be tracked and analyzed. Different parameters of the swimmers may be tracked continuously, such as distance being swam, swim pace, swim direction, exact path being swam including entry point to water and which lanes swimmer was in, path prediction, interaction with other swimmers, observation by other swimmers, or the like. In some exemplary embodiments, using a motion model, a prediction of where and when the swimmer should be in the near future may be performed.

In some exemplary embodiments, analyzing the swimmers may comprise determining a descriptor for each swimmer. The descriptor may comprise demographic or physiological information of the swimmers, such as gender, age group, height, weight, or the like. In some exemplary embodiments, the descriptor may be determined using machine learning techniques, computer vision techniques, or the like. As an example, the gender of the swimmer may be predicted using a deep learning classifier. As another example, the height of the swimmer may be determined using a distance calibrated camera based on measurement of the swimmer's torso length. As another example, the weight of the swimmer may be determined by proportions of different body parts relative to height, width and depth of the swimmer may be measured directly with calibration. It may be appreciated that some of the measurements may be required to be determined after the system is calibrated with respect to the visual input. As yet another example, an age group of the swimmer, such as between 0-3, 4-10, 11-18, above 18, or the like, may be determined using a classifier that determined the age group based on height and body proportions of the swimmer.

Additionally or alternatively, the descriptor may comprise information about the movement of the swimmer, such as type of action being performed, swimming style, or the like. An action that is currently being performed may be determined. Additionally or alternatively, a sequence of all previous actions, a predicted path of movement of the swimmer, motions aligned with tracked path of the swimmer, or the like, may be determined. In some exemplary embodiments, the descriptor may comprise a classification whether the swimmer is performing dynamic actions or static actions. A type of the dynamic actions, such as swimming, standing, lying, diving, playing, walking around the pool, or the like, may be determined. Additionally or alternatively, swimming speed and continuous swimming time and distance of each swimmer may be determined.

Additionally or alternatively, the descriptor may comprise interpreted analysis of the movement of the swimmer, such as swimming style (e.g., freestyle, breaststroke, backstroke, butterfly, or the like), quality of the swimming of the swimmer (e.g., beginner, intermediate, professional, or the like), or the like.

In some exemplary embodiments, analyzing the swimmers may comprise identifying a spotter observing one or more of the swimmers. The spotter may be a personal spotter observing a specific swimmer, a lifeguard in charge of the water area, or the like. The field of view of the spotter may be analyzed to determine which swimmers are observed by the spotter.

On Step 125, a risk level of each swimmer may be determined. In some exemplary embodiments, the risk level of each swimmer may be related to drowning potential of the each swimmer. The risk level of each swimmer may be determined based on the descriptor of the each swimmer, the presence of a spotter observing the swimmer, the field of view of the spotter, the location of the swimmer in the water area, or the like.

In some exemplary embodiments, each risk level may be associated with a different event severity. High severity events may occur to swimmers low risk level, and vice versa. The event severity may be determined on additional parameters in addition to the risk level of the swimmer, such as the location of the swimmer, external factors, or the like.

In some exemplary embodiments, potential distress situations may be situations that need to be investigated more than normal situations. Such situation may not necessarily need to be warranted an immediate alert to the emergency personal, but need to be investigated and verified. Such situations may be associated with higher severity level that cause the system to increase its sensitivity and give more focus to the event, in order to carefully monitor if the event is developing into an actual distress.

Examples of potential distress situations may be: a child in the water with no adults within about 3 meter radius, a child in the water without a floatation device, a person in water deeper than her own height, people running around the pool area, people entering into the water from non-regulated entry point, swimmers in an overcrowding area, age limit violation (e.g. children in hot tub), extended diving, or the like. Another example of a situation associated with potential distress may be when a group of people, most likely but not limited to children, who are playing and frolicking aggressively in and below the water with close contact between them, creating occlusions and splashing, is identified in the visual input. As yet another example of a situation associated with potential distress may be people jumping into the pool, especially in shallow water, especially if jumping on or near other people. Additionally or alternatively, potential distress situations may be determined when there is a mismatch between the swimmer and lane regulation, as an example, when a slow swimmer is detected in fast lane, a backstroke swimmer in freestyle lane, or the like.

In some exemplary embodiments, actual distress situations may be situations that can also occur in normal behavior, or associated with swimmers with a low risk level, but must be investigated by the emergency personnel in order to rule out true distress. Such situations may be associated with a higher severity that cause the system to increase its sensitivity and give more focus to the event, and help the emergency personnel. Examples of potential distress situations may be: erratic limb movement, motionless for long time, lying face down in the water, significant slowdown in swimming pace, especially in a swimming lane and for a swimmer who was previously swimming well; swimming direction not aligned with lane, swimming in "zig-zag", detection of a person in pool outside operating hours, or the like.

On Step 130, a non-uniform sensitivity level for drowning detection may be determined. In some exemplary embodiments, the system sensitivity may be a gauge for controlling the distribution of computational resources around the pool area. Events associated with high risk level may be handled with a higher sensitivity level.

In some exemplary embodiments, different sensitivity level for drowning detection may be handled with different levels of computational resources of the drowning detection system. Additional computational resources may be allocated to areas with a distress or drowning event, and according to the lifeguard attention map. Additionally or alternatively, different sensitivity level for drowning detection may be associated with different thresholds, such as a threshold which above certain computational resources are being used, a threshold at which a re-computation is performed, or the like.

As one example, different classifiers may be utilized to predict a likelihood of a potential drowning event. Events with a higher sensitivity level may be classified with classifiers utilizing increased computational resources, such as a higher number of features (e.g., a higher number of bins in a histogram, a higher number of directions of a gradient, or the like), features with a higher number of values, or the like.

As another example, events with a higher sensitivity level may be re-observed with a more accurate technologies, such as to obtain more descriptive visual input. The more descriptive visual input may be of a better resolution of images, a higher video frame rate, a smaller patch size, an input provided from different cameras observing different angles, or the like. A patch may be the atomic unit of image processing, the smaller the patch size the more detail and accuracy is obtained at the expense of processing power.

As yet another example, the rate at which descriptors and information is updated may be higher in areas with a higher sensitivity level. Such as the rate at which the visual input is obtained, the rate at which the analysis is performed, or the like.

Additionally or alternatively, a thresholds at which an alert is issued may be determined based on the sensitivity level of the system. An alert of a drowning event may be issued to an emergency personal, if the likelihood of the drowning event is above a predetermined threshold, such as above 50%, above 70%, or the like. Events with a higher sensitivity level may be alerted to the emergency personal even if their likelihood is lower.

Additionally or alternatively, different algorithms for determining the drowning events or alerting the events may be utilized based on the sensitivity level of the system. Algorithms with a higher accuracy may be utilized in events with a higher sensitivity level.

On Step 140, potential drowning events may be automatically detected. In some exemplary embodiments, the automatic detection may be performed by utilizing computational resources in a non-uniform manner. Increased computational resources may be applied with respect to swimmers or events with higher sensitivity level.

In some exemplary embodiments, Steps 110-140 may be periodically performed. On Step 145, a re-computation period may be set. The re-computation period may be a rate at which Step 140 is performed with respect to each swimmer. Swimmers with higher risk level may be inspected in a higher rate than other swimmers. Additionally or alternatively, only Steps 110 and 140 may be performed periodically.

On Step 150, an alert may be issued. In some exemplary embodiments, the alert may be issued in response to detecting a potential drowning event. The alert may be issued by sounding an audible alarm, giving textual signal or visual information, vibration alert, or the like. Additionally or alternatively, the alert may be issued by pointing towards the swimmer associated with the potential drowning event.

Figure 1B:
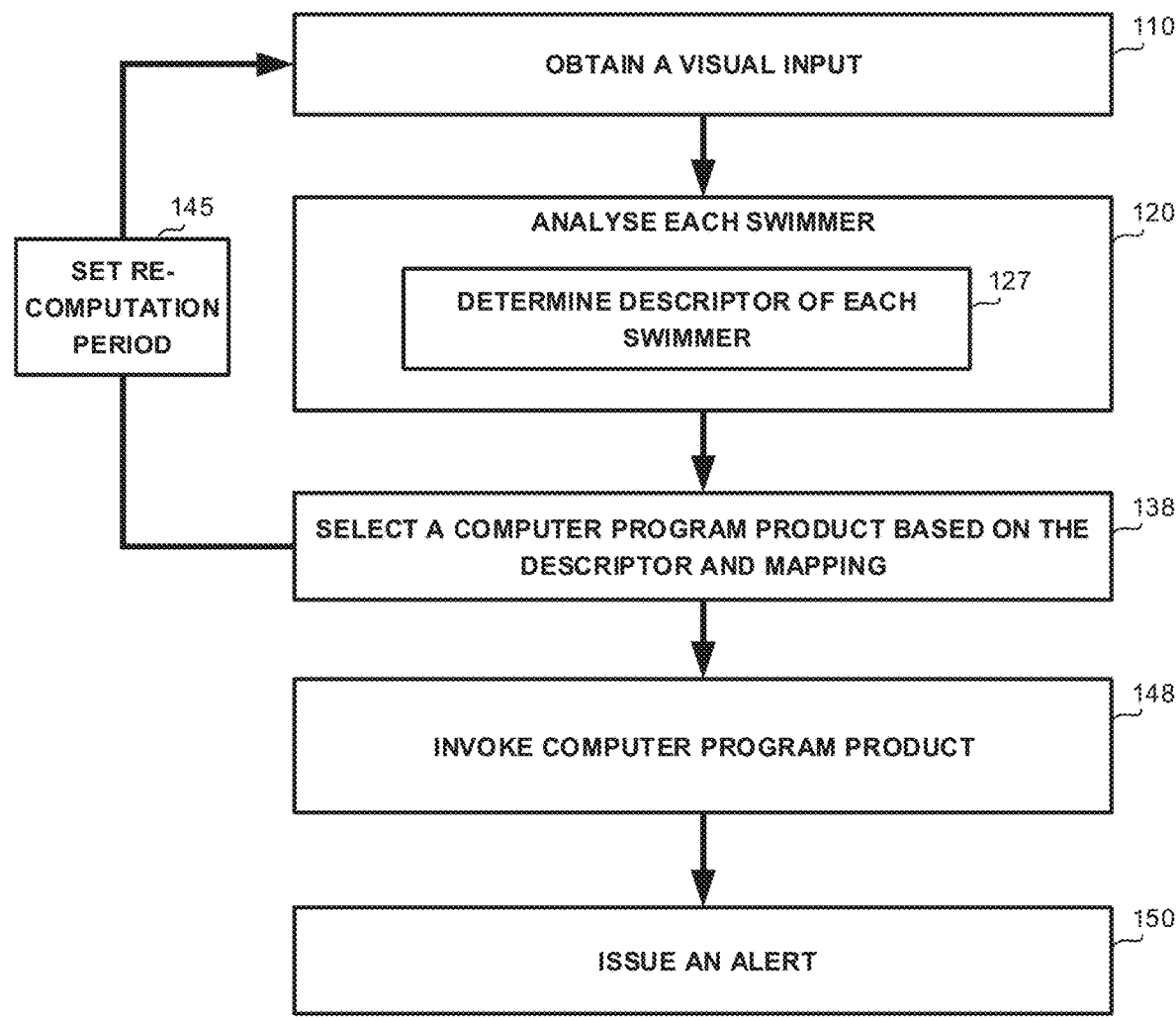

Referring now to FIG. 1B showing a flowchart diagram of a method, in accordance with some exemplary embodiments of the disclosed subject matter.

On Step 110, a visual input may be obtained.

On Step 120, each swimmer may be analyzed based on the visual input.

On Step 127, a descriptor may be determined for each swimmer. In some exemplary embodiments, the descriptor may be obtained based on the analysis of the swimmer in the visual input. As an example, the descriptor may comprise demographical features of the swimmer that may be determined based on the visual input, such as age or gender, or the like; external properties such as length, skin color, or the like; or the like. Additionally or alternatively, the descriptor may be further determined based on additional data associated with the swimmer that is not obtainable from the visual input, such as medical history, bathing habits, or the like. Such information may be obtainable from other resources, such as a pool membership database comprising information about members of the swimmers, historical information database, swimmers analytics database, or the like.

Additionally or alternatively, the descriptor may comprise a relative location of the swimmer in relation to a marker in the water area, such as the location of the swimmer with respect to a diving board, the location of the swimmer with respect to deep water area, the location of the swimmer with respect to tiles of specific colour in the floor, or the like. Additionally or alternatively, the descriptor may comprise properties of a portion of the water area in which the swimmer is located, such as depth of the water, crowdedness of the water area, or the like.

Additionally or alternatively, the descriptor may be determined based on interaction between the swimmer and a one or more other swimmers, such as the one or more other swimmers observing the swimmer, the swimmer aggressively playing with the one or more other swimmers, or the like.

It may be appreciated that the descriptor of the swimmer may be determined based on different types of information and properties of the swimmer, an aggregation of data, or the like.

On Step 170, a computer program product may be selected for each swimmer in the water area, based on the descriptor thereof. In some exemplary embodiments, the computer program product may be selected from a plurality of alternative computer program products implementing drowning detection. The selection may be performed in accordance with a mapping between swimmer descriptors and the plurality of alternative computer program products.

In some exemplary embodiments, the plurality of alternative computer program products may be based on a single configurable computer program product, having a plurality of alternative configurations. Each computer program product may be associated with a different configuration of the single configurable computer program product, such as different input, different thresholds, different drowning detection algorithm, different computations, or the like.

On Step 180, the computer program product selected for each swimmer may be invoked, in order to determine whether the swimmer is involved in a drowning event, what is the severity of the drowning event, whether to issue an alert, or the like. It may be appreciated that different drowning detection may be utilized for different swimmers.

In some exemplary embodiments, the selection of the computer program product may comprise selecting a configuration from a plurality of alternative configurations for a single configurable computer program product.

In some exemplary embodiments, different computer program products may be configured to utilize different classifiers for classifying drowning events. In some exemplary embodiments, different classifiers may be configured to implement a same classification algorithm, but to be trained with respect to different datasets. A computer program product utilizing a classifier that has been trained on a dataset comprising information about swimmers having at least one shared property with the swimmer may be selected. Such a selection may be performed based on the descriptor having the at least one shared property.

On Step 145, a re-computation rate may be determined. In some exemplary embodiments, Steps 110, 120, 127 and 138 may be repeatedly performed. The descriptor may be repeatedly re-computed, and based thereon, a selection of the computer program product may be modified. The re-computation rate may be determined based on a previously computed descriptor.

On Step 148, the computer program product selected for each swimmer may be invoked.

On Step 150, an alert may be issued in response to detecting a drowning event of a swimmer of interest. The drowning event may be identified by one of the plurality of alternative program products In some exemplary embodiments, the alert may be issued with respect to a configurable alert threshold. The configurable alert threshold may be based on the descriptor of the swimmer of interest.

Figure 1C:
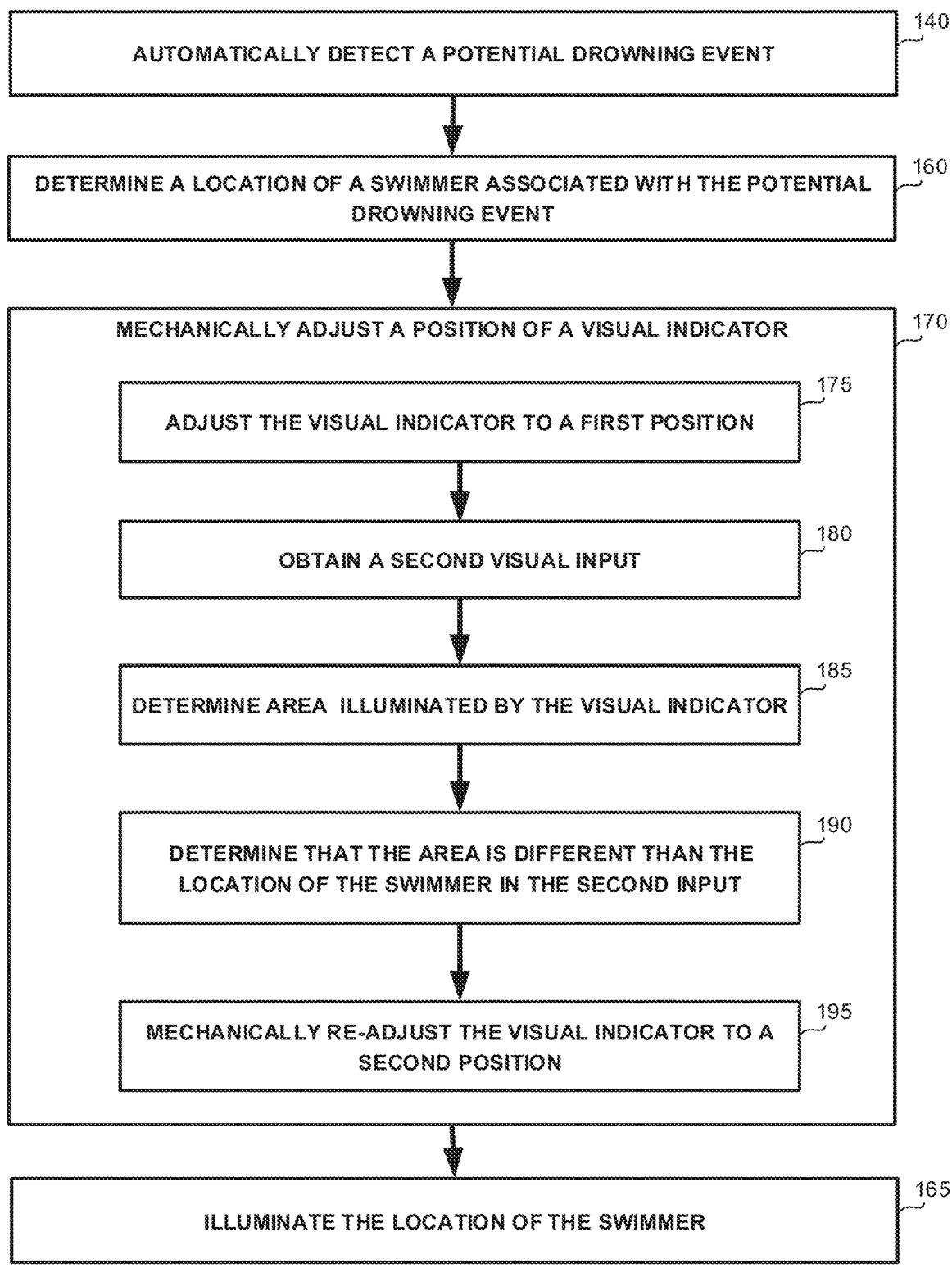

Referring now to FIG. 1C showing a flowchart diagram of a method, in accordance with some exemplary embodiments of the disclosed subject matter.

On Step 160, in response to automatically detecting a potential drowning event on Step 140, a location of a swimmer associated with the potential drowning event may be determined. In some exemplary embodiments, the location may be determined based on the visual input. In some exemplary embodiments, the swimmer may be continued to be tracked and the location may be continuously updated.

On Step 170, a position of a visual indicator may be mechanically adjusted. In some exemplary embodiments, the visual indicator may be configured to visually illuminate an area within the water area. The area may be illuminated by a light beam directed to a certain location in the water area, to a swimmer, or the like. Such a visual illumination may be configured to alert lifeguards, emergency personal, people in the water area, or the like; and point them towards the detected events. In some exemplary embodiments, the visual indicator may be a light projector, a laser projector or the like. These projectors may operate at a frequency and power which is safe to view, e.g. class 1 and 2 lasers. The visual indicator may comprise one laser light source for single-color projection, three sources for RGB (red, green, and blue) full color projection, or the like. In some exemplary embodiments, the visual indicator may be configured to illuminate with different colors indicating different levels of alert In some exemplary embodiments, the position of the visual indicator may be adjusted so that the visual indicator visually illuminates the location of the swimmer.

On Step 175, the visual indicator may be adjusted to a first position. In some exemplary embodiments, the visual indicator may be mounted above the water area to enable the illumination at any point in the pool without risk of occlusion. The visual indicator may be adjusted in accordance with a gimbal (e.g., a device like a gyroscope with motors which can electronically steer its direction). Additionally or alternatively, the visual indicator may comprise an actuator that is configured to move the visual indicator to a desired angle that allows to illuminate the desired location.

On Step 180, a second visual input may be obtained from the one or more cameras. The second visual input may comprise the area illuminated by the visual indicator. Additionally or alternatively, the second visual input may comprise information indicating the illuminated area, such as color differentiation, shadows, or the like.

On Step 185, a visually illuminated area within the water area may be identified. In some exemplary embodiments, the visually illuminated area may be illuminated by the visual indicator.

On Step 190, the visually illuminated area may be determined to be different than the location of the swimmer.

On Step 195, the visual indicator may be mechanically re-adjusted to a second position such that the visual indicator visually illuminates the location of the swimmer. In some exemplary embodiments, the visual indicator may be mechanically re-adjusted by moving lens or a laser light source, or the like; of the visual indicator to an angle that enables illuminating the location of the swimmer. Additionally or alternatively, the visual indicator may be moved (e.g., horizontally, vertically, or the like), in order to enable illumination the desired location.

On Step 165, the location of the swimmer may be illuminated by the visual indicator. As a result, the lifeguard or the emergency personal may be enabled to see the alert without losing eye contact with the water area. The lifeguard or the emergency personal may be directed to the source of the distress, e.g., the location of the drowning event, and can reach the swimmer faster.

Figure 2:
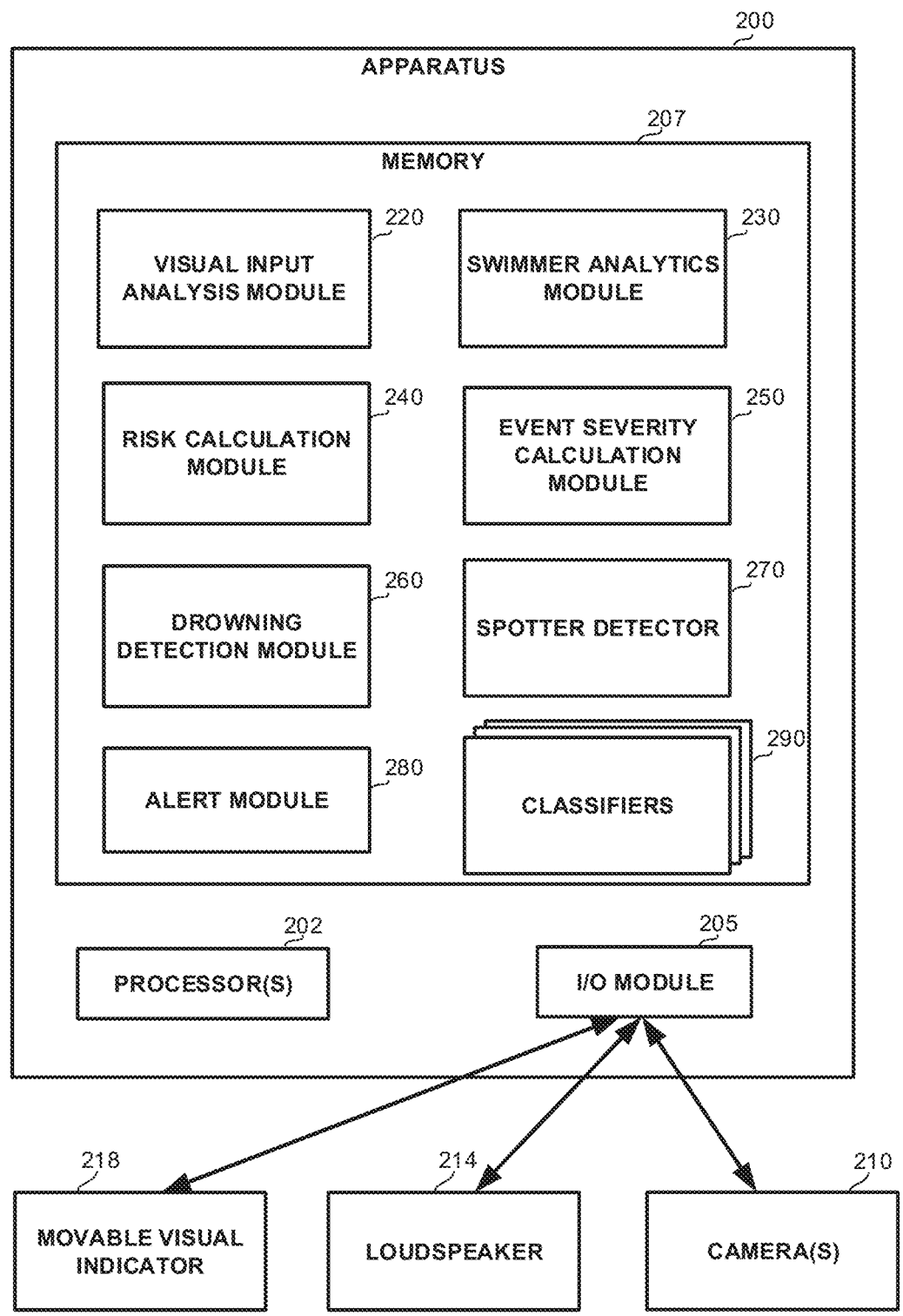
FIG. 2 shows a schematic illustration of an exemplary architecture, in accordance with some exemplary embodiments of the disclosed subject matter.

Referring now to FIG. 2 showing a block diagram of an apparatus, in accordance with some exemplary embodiments of the disclosed subject matter. An Apparatus 200 may be configured to support parallel user interaction with a real world physical system and a digital representation thereof, in accordance with the disclosed subject matter.

In some exemplary embodiments, Apparatus 200 may comprise one or more Processor(s) 202. Processor 202 may be a Central Processing Unit (CPU), a microprocessor, an electronic circuit, an Integrated Circuit (IC), a Graphical Processing Unit (GPU) or the like. Processor 202 may be utilized to perform computations required by Apparatus 200 or any of it subcomponents.

In some exemplary embodiments of the disclosed subject matter, Apparatus 200 may comprise an Input/Output (I/O) module 205. I/O Module 205 may be utilized to provide an output to and receive input from a user, such as, for example obtaining visual input from one or more cameras, such as Camera 210, issuing alerts through Loudspeaker 214, to issue visual indications through Movable Visual Indicator 218, sending messages to a personal screen such as to smart phones, screen, smart watches, or the like. [

In some exemplary embodiments, Apparatus 200 may comprise Memory 207. Memory 207 may be a hard disk drive, a Flash disk, a Random Access Memory (RAM), a memory chip, or the like. In some exemplary embodiments, Memory 207 may retain program code operative to cause Processor 202 to perform acts associated with any of the subcomponents of Apparatus 200. In some exemplary embodiments, Memory 207 may retain training data utilized to train one or more classifiers, and updated during the analysis.

In some exemplary embodiments, I/O Module 205 may be utilized to receive visual input from Camera 210. Camera 210 may be configured to observe a water area. In some exemplary embodiments, Camera 210 may be configured to be deployed out of the water, in order to detect a drowning event within the water area. Additionally or alternatively, Camera 210 may have additional designations not related directly to drowning detection. The visual input may be a video stream, a collection of photos, or the like. In some exemplary embodiments, Camera 210 may be configured to capture more than one path area at the same time, such as different pools, separated pools, adjacent parts of the same pool, or the like.

In some exemplary embodiments, I/O Module 205 may be utilized to receive specific information about the water area being observed, such as dimensions of each portion of the water area, water depth map, formal entry/exit points, operating hours, age limits, emergency personnel properties, or the like. The information may be obtained from a user (not shown) of Apparatus 200, based on input from Camera 210, or the like.

In some exemplary embodiments, the visual input may be provided to a Visual Input Analysis Module 220. Visual Input Analysis Module 220 may be configured to analyze the visual input and detect swimmers and other objects within the water area. In some exemplary embodiments, Visual Input Analysis Module 220 may be configured to extract information of the water area based on the visual input, such as pool dimensions, water depth map, formal entry and exit points, areas where diving is allowed, or the like.

In some exemplary embodiments, Swimmer Analytics Module 230 may be configured to analyze each swimmer detected in the water area by Visual Input Analysis Module 220. Swimmer Analytics Module 230 may be configured to analyze each swimmer independently from other swimmers. In some exemplary embodiments, Swimmer Analytics Module 230 may be configured to determine a descriptor for each swimmer, such as: demographic information, estimated swimming quality level, or the like.

In some exemplary embodiments, Risk Calculation Module 240 may be configured to determine a risk level of each swimmer. The risk level may be determined based on the descriptor of the swimmer. The risk level of each swimmer is related to drowning potential of the each swimmer.

In some exemplary embodiments, Event Severity Calculation Module 250 may be configured to determine a severity level of each detected event. The severity level may be determined based on the risk level the swimmer, location of the swimmer, behavior of other swimmers, or the like.

In some exemplary embodiments, Spotter Detector 270 may be configured to identify a spotter in the visual input. The spotter may be a personal spotter of associated with a single swimmer, or a lifeguard in charge of the whole water area. The spotter may be identified based on her activity over time, based on her field of view being focused on a certain area, swimmer, group of swimmers, or the like. The spotter may be identified based on her cloths, such as based on wearing a lifeguard uniform. A personal spotter may be identified based on activity, demographic, or the like, such as by identifying a parent of a child repeatedly observing the child. Additionally or alternatively, the spotter may be identified based on her reaching the water area together with the group of swimmers in her care. Spotter Detector 270 may be configured to determine a field of view of the spotter. Risk Calculation Module 240 may be configured to determine the risk level of swimmer observed by the spotter further based on the spotter observing thereof, based on the field of view of the spotter, or the like.

In some exemplary embodiments, Drowning Detection Module 260 may be configured to automatically detect potential drowning events. Drowning Detection Module 260 may be configured to utilize computational resources in a non-uniform manner. Drowning Detection Module 260 may be configured to apply increased computational resources with respect to events with high severity levels, and reduced computational resources with respect to events with low severity levels.

In some exemplary embodiments, Drowning Detection Module 260 may be configured to utilize visual inputs with different amounts of information in accordance with the risk level of the swimmer. The different visual inputs may differ in the resolution of images, rate of the video frame, patch sizes, which camera is capturing the visual input, the number of cameras capturing the visual input, or the like.

Additionally or alternatively, Drowning Detection Module 260 may be configured to determine a rate at which the automatic detection is performed with respect to specific swimmers. Higher rates may be determined for swimmers in higher risk levels.

In some exemplary embodiments, Drowning Detection Module 260 may be configured to utilize one or more Classifiers 290 to determine drowning events. Each of Classifiers 290 may be configured to predict a likelihood of a potential drowning event. Each of Classifiers 290 may be configured to utilize a different amount of computational resources, in accordance with the risk level. In some exemplary embodiments, each of Classifiers 290 may be configured to receive a different set of features. Classifiers associated with higher risk levels may be configured to receive sets of greater number of features than the others. Additionally or alternatively, classifiers associated with higher risk levels may be configured to utilize features with greater detail, e.g. by using a greater number of potential values than features representative of a same trait utilized by the other classifiers. In some exemplary embodiments, a Cartesian product of the features may provide a set of potential depictions by a set of features. In case the set of potential depictions is larger, then it comprises more information. The set of potential depictions may increase if additional features are added, or if the features are of greater detail, e.g., associated with a larger domain of values from which the value of an assignment to the feature is picked.

In some exemplary embodiments, Drowning Detection Module 260 may be configured to apply one of Classifier 290 with respect to a certain swimmer, in accordance with the risk level determined for the swimmer. The classifier may be configured to predict the likelihood of drowning of the swimmer. Additionally or alternatively, Drowning Detection Module 260 may be configured to apply one of Classifier 290 with respect to a certain event, in accordance with the severity of the event.

Additionally or alternatively, Drowning Detection Module 260 may be configured to utilize different thresholds at which events are alerted, different algorithms that are used to determine event severity, or the like.

In some exemplary embodiments, Alert Module 280 may be configured to issue an alert when a drowning event is detected by Drowning Detection Module 260. In some exemplary embodiments, Alert Module 280 may utilize I/O Module 205 provide an alert signal to Loudspeaker 214, Movable Visual Indicator 218, or the like. In some exemplary embodiments, Loudspeaker 214 may be configured to convert the alert signal into a corresponding sound that inform lifeguards or people in the water area about the drowning event. Additionally or alternatively, Alert Module 280 may be configured to issue a textual, audible or visual information on a monitor, such as in the lifeguard station, on a smartphone of the lifeguard, on a smart watch allocated to the lifeguard, with an earpiece worn by the lifeguard, on a screen in the water area, or the like. The signal may be configured to point on the distress on a diagram of the pool or the water area. Such a signal may inform the lifeguard about the drowning event, a distress situation, a potential distress situation, or the like. The signal can convey information about the location and type of situation reported.

Additionally or alternatively, Movable Visual Indicator 218 may be configured to indicate the location of the drowning event. Movable Visual Indicator 218 may be a laser pointer, or any other type of visual pointer. Movable Visual Indicator 218 may be configured to directly point towards the person in distress. When the lifeguard is reacting to the distress, she can follow the signal of Movable Visual Indicator 218 to reach the person. Movable Visual Indicator 218 may be configured to continue tracking the person so the lifeguard does not need to look away from the pool to some external device. In some exemplary embodiments, Camera 210 may be utilized to re-adjusted Movable Visual Indicator 218, to enable locating Movable Visual Indicator 218 in a correct location.

Figure 3A:
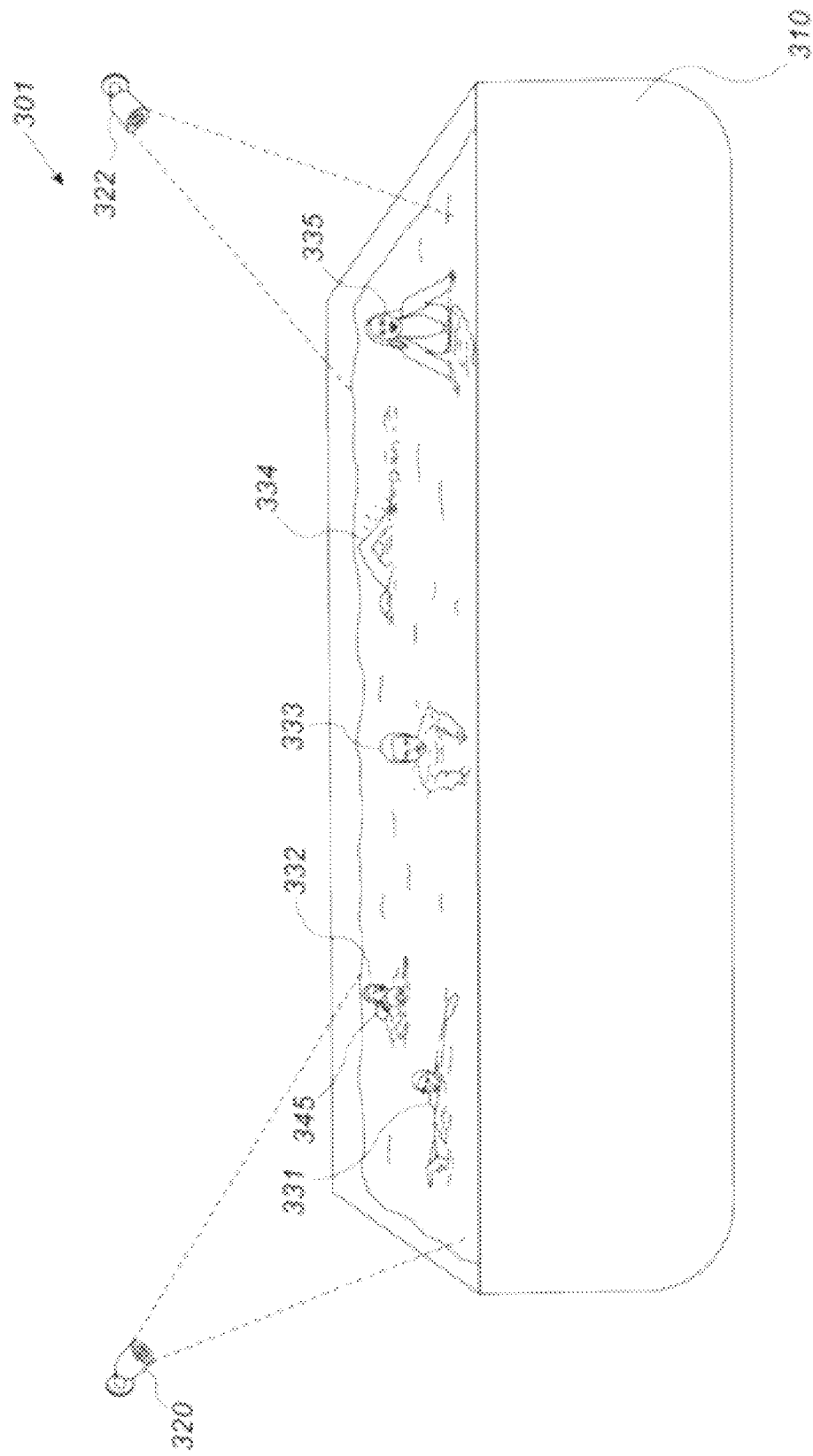
FIGS. 3A-3C show schematic illustrations of environments, in accordance with some exemplary embodiments of the disclosed subject matter.

Referring now to FIG. 3A showing a schematic illustration of an environments, in accordance with some exemplary embodiments of the disclosed subject matter.

In some exemplary embodiments, an Area 301 may comprise a Pool 310. Pool 310 may be observed by a plurality of cameras that are deployed out of the water, such as Camera 320 and Camera 322. In some exemplary embodiments, visual input of Pool 310 and swimmers bathing therein may obtained from the plurality of cameras. In some exemplary embodiments, one or more of the plurality of cameras may be out-of-water cameras such as Camera 320 and Camera 322. In some cases, the portions may be non-overlapping. In other cases, the portions may overlap. Additionally or alternatively, other types of cameras (not shown) may be deployed, such as in the water camera, floating camera, smart-phone cameras, or the like. Each camera may be in charge of monitoring a different portion of Pool 310. Each camera may be in charge of monitoring a different portion of Pool 310. In some exemplary embodiments, geometric triangulation from multiple cameras may not be required, as each camera may be positioned to provide the visual input relating to different and separate portions of the water area. It may be appreciated that other types of cameras (not shown) may be deployed, such as underwater cameras, thermal cameras, infra-red cameras, floating camera, smart-phone cameras, or the like. However, in some cases, such cameras may be used to augment the disclosed subject matter. Additionally or alternatively, additional imaging devices and technologies may be utilized to obtain the visual input, such as sonar systems, radar systems, or the like.

As an example, Camera 320 may be an overhead camera that is located substantially above Pool 310. Camera 320 may be positioned outside of the water and observing all over Pool 310. As another example, Camera 320 and Camera 322 may be non-centered cameras positioned with an angle to the water Camera 320 may be configured to observe the left portion of Pool 310, while Camera 322 may be configured to observe the right portion of Pool 310.

In some exemplary embodiments, a plurality of swimmers may be bathing in Pool 310, such as Swimmers 331-335. Each swimmer may be swimming in a different portion of Pool 310, in a different position, in different body motions, swimming in different styles, or the like. As an example, Swimmer 335 may be standing in Pool 310, Swimmer 334 may be front crawling, or the like. Each swimmer in Area 301 may be tracked and analyzed independently from other swimmers. Different parameters of the swimmers may be tracked continuously, such as distance being swam, swim pace, swim direction, exact path being swam including entry point to water and which lanes swimmer was in, path prediction, or the like. In some exemplary embodiments, using a motion model, prediction of where and when the swimmer should be in the near future may be performed.

In some exemplary embodiments, the system may be fed with specific information about Pool 310, such as pool dimensions, water depth map, formal pool entry/exit points, operating hours, age limits (e.g. hot tub), lane restrictions and guidelines (fast vs. slow, swim style), lifeguard clothing (e.g. shirt, hat), pool operating hours, or the like. The information may be obtained from an operator of the system. Additionally or alternatively, the information may be extracted from visual input obtained from Camera 320 and Camera 322.

In some exemplary embodiments, descriptor of each swimmer may be determined. The descriptor may comprise demographic information of the swimmers, such as gender, age group, height, or the like. As an example, based on the height and body proportions, Swimmers 331 and 332 may be determined to be in an age group of children, while Swimmers 333, 334 and 335 may be determined as adults. As another example, the gender of Swimmer 335 may be predicted to be female based on body proportions, hairstyle, type of clothing's, or the like.

Additionally or alternatively, the descriptor of each swimmer may comprise estimated swimming quality level. The estimated quality level may be determined based on action currently being performed by the swimmer, history of previous actions of the swimmer, tracked path of the swimmer, or the like. As an example, a specific swimming style of the swimmer may be determined. Each swimming style may be associated with a different level of swimming quality (e.g., advanced swimming style may be associated with a higher quality swimming and accordingly with a lower risk level). As another example, Swimmer 333 may be determined to be diving in place, based on Swimmer 333 moving up and down without horizontal movement.

Additionally or alternatively, the descriptor may comprise information that is not obtainable from the current visual input, such as medical history, bathing habits, or the like. Such a descriptor may be obtainable from other resources, such as a pool membership database comprising information about members of the swimmers, historical information database, swimmers analytics database, or the like.

In some exemplary embodiments, a risk level of each swimmer may be determined based on the analysis. The risk levels may be in accordance with distress level that the swimmers are likely to be associated with. The lower risk level may be for swimmers with non-potential risk at all, such as athletics, professional swimmers, swimmers swimming at a fast pace, swimmers outside the pool, or the like. The next risk level may be for swimmers in a potential risk, such as swimmers jumping into the water, behaving aggressively, using floatation devices, swimming in water deeper than own height, or the like. The highest risk level may be for swimmers that are most likely to be in actual distress or drowning situation. Additional risk levels may be located between the lowest risk level and the highest risk level, in accordance with potential risk of the swimmers, based on the system's classification, or the like.

In some exemplary embodiments, an event severity may be determined for each possible event based on the analysis. The event severity may be determined based on the risk level of the swimmer associated with the event, with respect to other features of the events.

As an example, Swimmer 331 and Swimmer 332 may be children swimming in the water with no adults within a predetermined radius, such as about 2 meters radius, about 3 meters radius, about 5 meters radius, or the like. Swimmer 331 and Swimmer 332 may be in a potential distress situation (e.g., a high severity) because of being in a high risk level. Child Swimmer 331 may be assigned with a higher risk level than child Swimmer 332, as child Swimmer 332 is equipped with a Floating Device 345. As another example, Swimmer 335 may be in a potential distress situation for being in a water deeper than her own height, Swimmer 334 may be in a potential distress situation for being extendedly diving, or the like. As yet another example, Swimmer 333 may be classified as in safe situation with the lower risk level.

In some exemplary embodiments, computational resources may be utilized in a non-uniform manner in order to automatically detect potential drowning events. As an example, increased computational resources may be applied with respect to Swimmer 331, and a reduced computational resources with respect to Swimmer 333. Computational resources applied with respect to Swimmer 335 may be higher than the computational resources applied with respect to Swimmer 333, but lower than the computational resources applied with respect to Swimmer 334.

In some exemplary embodiments, a classifier may be utilized to predict a likelihood of a potential drowning event for each swimmer. Different classifiers may be utilized for different risk levels. Each classifier may be configured to utilize a different amount of computational resources with respect to the risk level. Classifiers utilized in higher risk levels may be configured to utilize increased computational resources, while classifiers associated with a lower risk level may be configured to utilize lower amounts of computational resources. As an example, a classifier utilizing reduced computational resources may be utilized to automatically detect drowning events associated with Swimmer 334, comparing with the classifier utilized to automatically detect drowning events associated with Swimmer 331.

In some exemplary embodiments, each classifier may be configured to receive a set of features. The classifier may be configured to predict the likelihood of the drowning events based on the values of the features. Different classifiers may be configured to utilize different features sets. Classifiers utilized in higher risk levels may be configured to utilize larger sets of features to enable the prediction to be more accurate, to identify extreme cases, or the like. As an example, for child Swimmer 331 and Swimmer 332, a classifier utilizing a set of features with a number of features greater than the others may be utilized. The set of features in this case may comprise features that are relevant to detecting drowning for children, such as the use of floating devices, specific gesture analysis, or the like.

Additionally or alternatively, different sets of features may comprise different features that are representative of a same trait but have different numbers of potential values. Classifiers utilized in higher risk levels may be configured to utilize sets of features comprising the feature with the greater detail, e.g. with a greater number of potential values than the others.

In some exemplary embodiments, Camera 320 and Camera 322 may be configured to provide different types of visual input. The different types of visual inputs may differ in the resolution of images, the video frame rate, the patch size, or the like. Additionally or alternatively, Camera 320 and Camera 322 may be configured to provide updated visual inputs in different rates. As an example, Camera 320 may be configured to provide more accurate input in a higher rate. Input from Camera 320 may be utilized to determine a potential drowning event with respect to swimmers in higher risk levels. Additionally or alternatively, input from the two cameras may be utilized to determine a potential drowning event with respect to swimmers in higher risk levels; while input from a single camera may be utilized to determine a potential drowning event with respect to swimmers in lower risk levels.

Figure 3B:
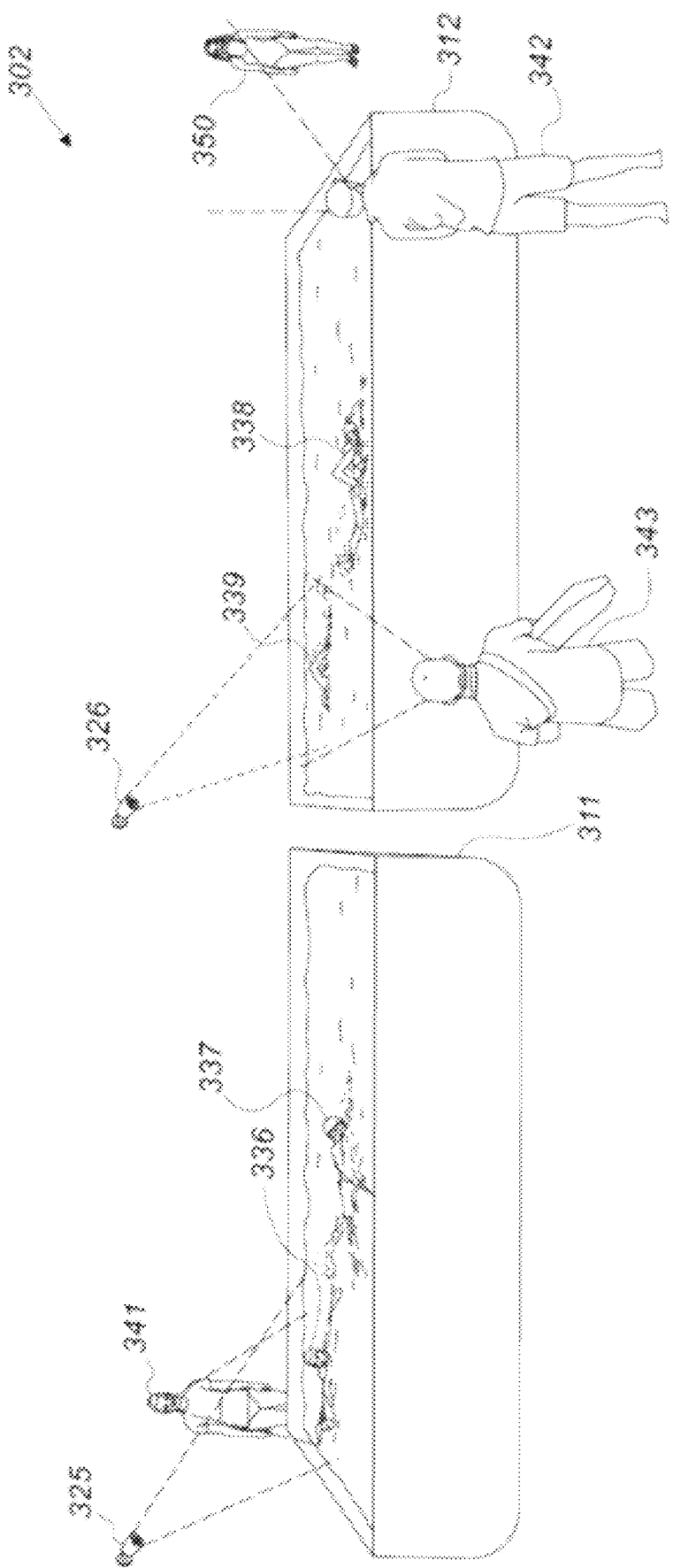

Referring now to FIG. 3B showing a schematic illustration of an environments, in accordance with some exemplary embodiments of the disclosed subject matter.

In some exemplary embodiments, an Area 302 may comprise a Pool 311 and a Pool 312. Area 302 may be observed by a plurality of cameras that are deployed out of the water, such as Camera 325 and Camera 326. In some exemplary embodiments, visual input of Area 302 and swimmers bathing therein may obtained from the plurality of cameras. In some exemplary embodiments, Camera 325 and Camera 326 may be similar to Camera 320 and Camera 322. In some exemplary embodiments, each camera may be in charge of monitoring a different portion of Area 302. As an example, Camera 325 may located substantially above Pool 311 and utilized to observe Pool 311, while Camera 326 may located substantially above Pool 312 and may be in charge of monitoring Pool 312.

In some exemplary embodiments, a plurality of swimmers may be bathing in Area 302, such as Swimmers 336-337 that are swimming on Pool 311, Swimmer 338-339 that are swimming in Pool 312, Woman 350 walking outside Pool 312, or the like. Each person in Area 302 may be tracked and analyzed independently from other people. (Similarly to the analysis of the swimmers in FIG. 3A).

In some exemplary embodiments, the system may be configured to analyze Area 302 including the water areas (e.g., Pool 311 and Pool 312) and the area surrounding the pools.

In some exemplary embodiments, a Spotter 341 may be observing a Swimmer 336. Spotter 341 may be a personal spotter of Swimmer 336, such as her mother, accompanist, or the like. Spotter 341 may be supposed to watch over Swimmer 336 and may not necessarily be in charge of watching other swimmers. The risk level of the Swimmer 336 may be determined further based on Spotter 341 observing her. The existence of a personal spotter reduced the risk of drowning of Swimmer 336. The risk level may be lower than the risk level determined if no personal spotter was observing Swimmer 336. In such a case, the system may utilize its computational resources to observe other portions of Area 302.

In some exemplary embodiments, a Spotter 343 may be observing Swimmer 339 and other swimmers. Spotter 343 may be a lifeguard in charge of Area 302. Spotter 343 may be supposed to observe all of the swimmers in Area 302. However, the human capability of Spotter 343 may be limited, and only swimmers in the field of view of Spotter 343 may be observed.

In some exemplary embodiments, large water areas, such as Area 302, may have a plurality of lifeguards in charge of observing thereof, such as Spotter 342 and Spotter 344. Each spotter may be supposed to observe different portions Area 302. Additionally or alternatively, both of Spotter 342 and Spotter 343 may be supposed to watch all of Area 302 together, in order to increase the safety, such as by adding an additional pair of eyes watching the swimmers, covering each other when one is watching in a certain direction, or the like.

In some exemplary embodiments, the system may be configured to identify each spotter in Area 302, such as Spotter 341, Spotter 342, Spotter 343, or the like. The system may be configured to determine a field of view of each spotter during the analysis of the visual input and the analysis of the swimmer. Based on a swimmer being in the field of view of a spotter, the risk level thereof may be reduced. Additionally or alternatively, in some cases, if Spotter 343, for example, is observing Swimmer 339 for a long time (such as for several minutes), inspecting the same swimmer several times, or the like, Swimmer 339 may be indicated to be in a distress. The risk level of Swimmer 339 may be increased, and additional computational resources of the system may be incited to watch Swimmer 339. On the other hand, when a spotter is busy observing a certain swimmer, other swimmers who are supposed to be in the response of this spotter may be in a higher risk level, for no lifeguard watching them. As a result, the risk level of Swimmer 338 may be higher than the risk level of Swimmer 339.

Additionally or alternatively, Spotter 342 may be busy watching a Person 350 outside Pool 342. The system may be configured to identify that Spotter 342 is distracted, and accordingly increasing the risk level in the area in charge of Spotter 342. Furthermore, the system is configured to distinguish between cases that a spotter is watching a swimmer, such as Spotter 343 watching Swimmer 339, and cases that a spotter is watching an irrelevant person, such as Spotter 342 being distracted by Person 350. The system may be configured to computationally learn what features are associated with each of case, such as the swimmer/person being inside of the pool, the age or gender of the swimmer/person, external characters of the swimmer/person, or the like.

Figure 3C:
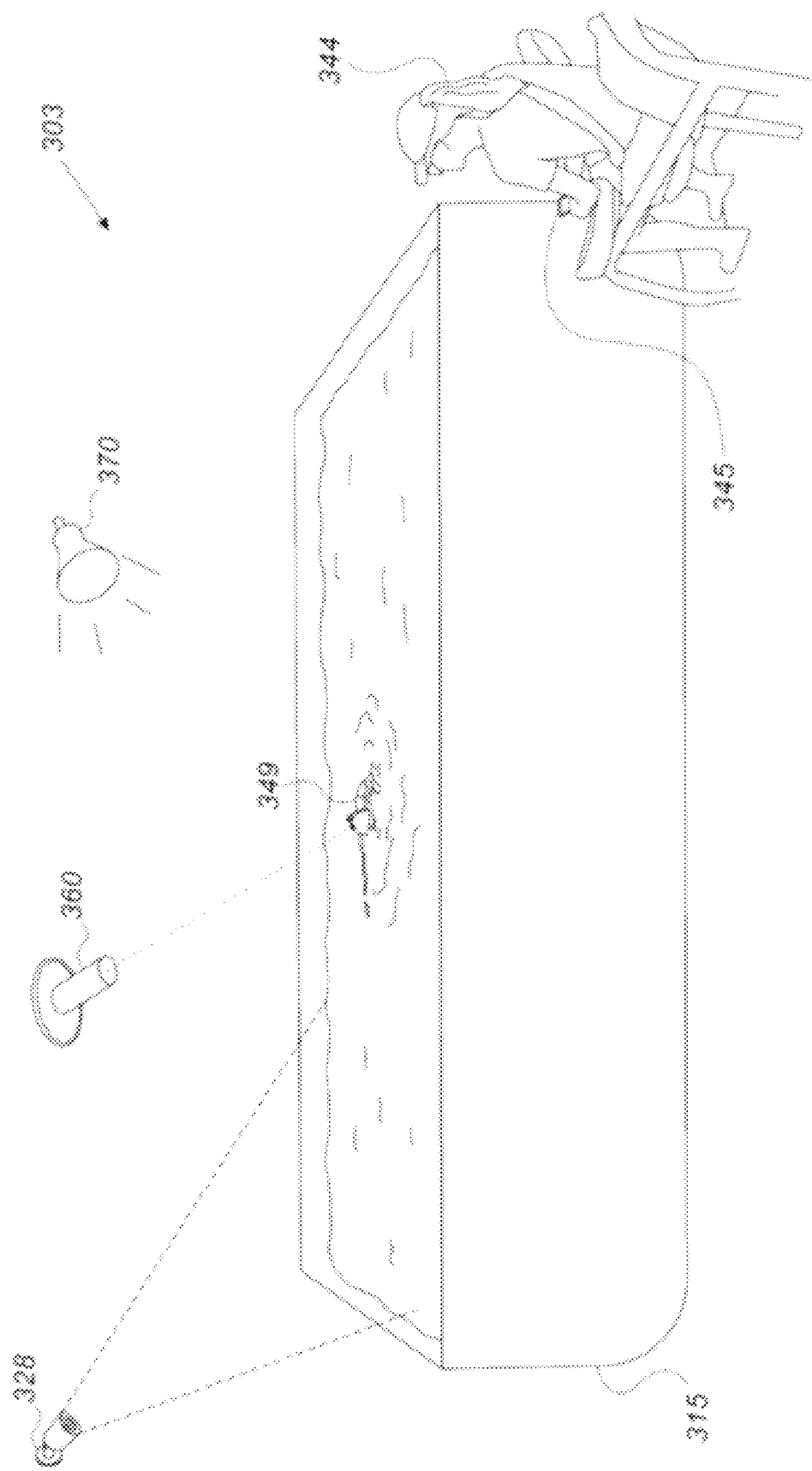

Referring now to FIG. 3C showing a schematic illustration of an environments, in accordance with some exemplary embodiments of the disclosed subject matter.

In some exemplary embodiments, an Area 303 may comprise a Pool 315. Pool 315 may be observed by one or more cameras that are deployed out of the water, such as Camera 328. In some exemplary embodiments, visual input of Pool 315 and swimmers bathing therein may obtained from Camera 328. The visual input may be analyzed, to identify swimmers and spotters, determine their properties, and determining the risk level of each swimmer in Area 303.

In some exemplary embodiments, a Swimmer 349 may be identified in Pool 315. Swimmer 349 may be determined to be a distress situation. The sensitivity level for drowning detection of Swimmer 349 may be increased. Increased computational resources of the system may be deployed to observe Swimmer 349 and detect whether Swimmer 349 is potentially drowning. Additionally or alternatively, algorithms with a higher accuracy, lower thresholds, or the like, may be utilized with respect to Swimmer 349.

In some exemplary embodiments, in response to automatically detecting that Swimmer 349 is drowning, the system may issue an alert to Emergency Personnel 344 indicating the potential drowning event.

In some exemplary embodiments, a Visual Indicator 360 may be configured point towards Swimmer 349. Visual Indicator 360 may assist Emergency Personnel 344 locate the drowning event, and follow Swimmer 349. Visual Indicator 360 may be a single beam laser pointer, a multi beam laser pointer, a projector, or the like. Visual Indicator 360 may be configured to point with different colors indicating different levels of alert or distress. As an example, Visual Indicator 360 may point with red color to indicate actual drowning events, green for potential drowning, blue for potential distress, or the like. Visual Indicator 360 may be mounted above Pool 315, in a substantially high location in Area 303, or the like; in order to be able to create a light beam directed at any point in Pool 315 without the risk of occlusion. Visual Indicator 360 may be configured to indicate the location of the drowning event by directly pointing towards Swimmer 349. When Emergency Personnel 344 reacts to the distress, she can follow the signal of Visual Indicator 360 to reach Swimmer 349. Visual Indicator 360 may be configured to continue tracking the person so the lifeguard does not need to look away from the pool to some external device.

In some exemplary embodiments, Visual Indicator 360 may be movable. As an example, Visual Indicator 360 may be mounted on a device, such as a gyroscope with motors (not shown). The device may be configured to steer the direction of Visual Indicator 360. Additionally or alternatively, the indication of Visual Indicator 360 may be adjusted in accordance Camera 328, based on motion prediction of the swimmer, or the like; to enable locating Visual Indicator 360 in a correct location.

Additionally or alternatively, a Loudspeaker 370 may be configured to issue a sound alert indicating the drowning event.

Additionally or alternatively, a textual or visual or audible information on the drowning event may be provided to Personnel Emergency 344. The information may be provided on a Device 345 visible to Personnel Emergency 344, such as a smartphone, a screen, earpiece, headphones, watch, or the like. The information may be configured to point on the drowning event on a diagram of Pool 315 or Area 303. The information may be configured to inform Personnel Emergency 344 the drowning event, the location of Swimmer 349, or the like. Additionally or alternatively, an auditory alert or auditory information may be provided to Personnel Emergency 344, such as via Device 345, via earphones connected to Device 345, or the like.

It may be appreciated that Visual Indicator 360 and Loudspeaker 370 may be configured to alert other people in Area 303 of the potential drowning event, and not only Loudspeaker 370.

Figure 4:
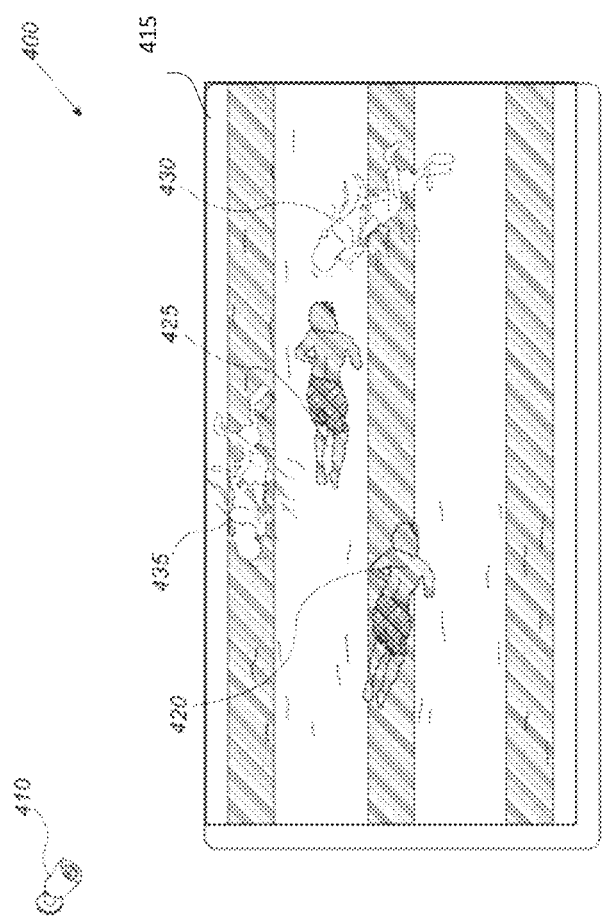
FIG. 4 shows a schematic illustration of an environment, in accordance with some exemplary embodiments of the disclosed subject matter.

Referring now to FIG. 4 showing a schematic illustration of an environment, in accordance with some exemplary embodiments of the disclosed subject matter.

In some exemplary embodiments, a Water Area 400 may comprise a Pool 415. Pool 415 may be observed by one or more cameras that are deployed out of the water, such as Camera 410. In some exemplary embodiments, visual input of Pool 415 and swimmers bathing therein may obtained from Camera 410. The visual input may be analyzed, to identify swimmers and spotters, determine their properties, and determining a descriptor of each swimmer in Area 400.

In some exemplary embodiments, floor of Pool 415 may be colored in dark and light strips, defining different swimming paths.

In some exemplary embodiments, a dark-skinned Swimmer 420 and a light-skinned Swimmer 430 may be identified in Pool 415. Different swimmer descriptors may be determined for Swimmer 420 and Swimmer 430 based on their skin tone. Accordingly, different computer program products for drowning detection, such as different classifiers, may be invoked for Swimmer 420 and Swimmer 430.

In some exemplary embodiments, Swimmer 420 may be detected swimming in a dark background water area. Additionally or alternatively, Swimmer 425 (same as Swimmer 420) may be detected swimming in a light background area. Similarly, Swimmer 430 may be detected in light background water area, two-colored water area, or the like. Swimmer 435 (same as Swimmer 430) may be detected in a dark background water area. Swimmers swimming in area with background similar to their skin tone, may be more difficult to be observed and analyzed for drowning detection. As a result, different swimmer descriptor may be determined for similar Swimmer 420 and Swimmer 425 based on swimming in water area being in different background colors.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for drowning detection based on swimmer analytics, the method comprising:
obtaining a visual input from one or more cameras observing a water area;
analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources;
wherein said automatically detecting comprises comparing a confidence measurement of a detection algorithm with a respective threshold in order to determine existence of a potential drowning event; and wherein said utilizing computational resources in a non-uniform manner comprises setting a first threshold with respect to the first swimmer and a second threshold with respect to the second swimmer, wherein the first threshold is lower than the second threshold, whereby a same detected potential event having a confidence measurement between the first threshold and the second threshold is configured to be reported with respect to the first swimmer but not with respect to the second swimmer, whereby computational resources utilized with relation to the first swimmer are increased with respect to computation resources utilized with relation to the second swimmer.

2. The method of claim 1, wherein the risk level of each swimmer is related to drowning potential of the each swimmer.

3. The method of claim 1,
wherein said analysing comprises determining a descriptor for each swimmer, wherein the descriptor comprises at least one of the following: demographic information, an estimated swimming quality level, a behaviour descriptor of the each swimmer in the water area, and an interaction descriptor of the each swimmer with other swimmers in the water area; and
wherein the risk level of each swimmer is determined based on the descriptor of the each swimmer.

4. The method of claim 1,
wherein said analysing comprises extracting descriptor about the each swimmer from a database, wherein the descriptor comprises at least one of the following: medical information and depiction of normal swimming activity; and
wherein the risk level of each swimmer is determined based on the descriptor of the each swimmer.

5. The method of claim 1, wherein said determining the risk level of the each swimmer comprises determining a location of the each swimmer, retrieving a risk level of the location of the each swimmer, wherein the risk level of the each swimmer is based on the risk level of the location of the each swimmer.

6. The method of claim 1, wherein the first set of features comprises a first feature, wherein the second set of features comprises a second feature, wherein the first feature and the second feature are representative of a same trait, wherein a number of potential values of the first feature is greater than a number of potential values of the second feature.

7. The method of claim 1, wherein said automatically detecting comprises applying a detection algorithm for the first and second swimmers periodically, wherein said applying comprises applying the detection algorithm at a first rate for the first swimmer and applying the detection algorithm at a second rate for the second swimmer, wherein the first rate is higher than the second rate.

8. A method for drowning detection based on swimmer analytics, the method comprising:
obtaining a visual input from one or more cameras observing a water area;
analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources;
wherein said automatically detecting comprises:
obtaining a first visual input with respect to the first swimmer;
obtaining a second visual input with respect to the second swimmer, wherein the first visual input comprises more information than the second visual input;
utilizing the first visual input in order to determine a potential drowning event with respect to the first swimmer; and
utilizing the second visual input in order to determine a potential drowning event with respect to the second swimmer.

9. The method of claim 8,
wherein the first and second visual inputs differ in at least one of the following: a resolution of images, a video frame rate, a patch size.

10. A method for drowning detection based on swimmer analytics, the method comprising:
obtaining a visual input from one or more cameras observing a water area;
analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources; and
wherein said obtaining and said automatically detecting are performed periodically, wherein a rate at which said automatically detecting is performed with respect to the first swimmer is higher than a rate at which said automatically detecting is performed with respect to the second swimmer.

11. A method for drowning detection based on swimmer analytics, the method comprising:
obtaining a visual input from one or more cameras observing a water area;
analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources; and
wherein said analyzing comprises identifying a spotter observing the second swimmer, wherein said determining the risk level of the second swimmer is based on the spotter observing the second swimmer.

12. The method of claim 11,
wherein the spotter is one of the following:
a personal spotter of the second swimmer; and
a lifeguard in charge of the water area.

13. A method for drowning detection based on swimmer analytics, the method comprising:
obtaining a visual input from one or more cameras observing a water area;
analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources; and
wherein said analyzing comprises identifying a spotter, determining a field of view of the spotter, and wherein said determining the risk level is performed based on the field of view of the spotter.

14. The method of claim 1, wherein the water area comprises a first water area and a second water area, wherein the first and the second water areas are separated, wherein the first swimmer is located in the first water area and the second swimmer is located in the second water area.

15. The method of claim 1, in response to said automatically detecting a potential drowning event:
determining a location of a swimmer associated with the potential drowning event; and
mechanically adjusting a position of a visual indicator configured to visually illuminate an area within the water area, wherein said mechanically adjusting comprises adjusting the position so that the visual indicator visually illuminates the location of the swimmer.

16. A method for drowning detection based on swimmer analytics, the method comprising:
obtaining a visual input from one or more cameras observing a water area;
analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources;
in response to said automatically detecting a potential drowning event:
determining a location of a swimmer associated with the potential drowning event;
mechanically adjusting a position of a visual indicator configured to visually illuminate an area within the water area, wherein said mechanically adjusting comprises adjusting the position so that the visual indicator visually illuminates the location of the swimmer;
wherein said mechanically adjusting comprises:
adjusting the visual indicator to a first position;
obtaining a second visual input from the one or more cameras;
determining a visually illuminated area within the water area, wherein the visually illuminated area is illuminated by the visual indicator;
determining that the visually illuminated area is different than the location of the swimmer; and mechanically re-adjusting the visual indicator to a second position, wherein in the second position the visual indicator visually illuminates the location of the swimmer.

17. The method of claim 1, wherein said utilizing computational resources in a non-uniform manner comprises applying a first algorithm to detect a potential drowning event of the first swimmer and applying a second algorithm to detect a potential drowning event of the second swimmer, wherein the second algorithm is configured to utilize less computational resources than the first algorithm.

18. The method of claim 17, wherein the first algorithm has a reduced likelihood of having a false negative detection of potential drowning events in comparison to the second algorithm.

19. A computerized apparatus having a processor, the processor being adapted to perform the steps of:
   obtaining a visual input from one or more cameras observing a water area;
   analyzing each swimmer in the water area based on the visual input from the one or more cameras, wherein said analyzing comprises determining a risk level of each swimmer, whereby a first risk level is determined for a first swimmer and a second risk level is determined for a second swimmer, wherein the first risk level is higher than the second risk level; and
   automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources;
   wherein said automatically detecting comprises comparing a confidence measurement of a detection algorithm with a respective threshold in order to determine existence of a potential drowning event; and
   wherein said utilizing computational resources in a non-uniform manner comprises setting a first threshold with respect to the first swimmer and a second threshold with respect to the second swimmer, wherein the first threshold is lower than the second threshold, whereby a same detected potential event having a confidence measurement between the first threshold and the second threshold is configured to be reported with respect to the first swimmer but not with respect to the second swimmer, whereby computational resources utilized with relation to the first swimmer are increased with respect computation resources utilized with relation to the second swimmer.

20. A computerized apparatus having a processor, the processor being adapted to perform the steps of:
   obtaining a visual input from one or more cameras observing a water area;
   analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
   automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources;
   wherein said automatically detecting comprises:
      obtaining a first visual input with respect to the first swimmer;
      obtaining a second visual input with respect to the second swimmer, wherein the first visual input comprises more information than the second visual input;
      utilizing the first visual input in order to determine a potential drowning event with respect to the first swimmer; and
      utilizing the second visual input in order to determine a potential drowning event with respect to the second swimmer.

21. A computerized apparatus having a processor, the processor being adapted to perform the steps of:
   obtaining a visual input from one or more cameras observing a water area;
   analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
   automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources; and
   wherein said obtaining and said automatically detecting are performed periodically, wherein a rate at which said automatically detecting is performed with respect to the first swimmer is higher than a rate at which said automatically detecting is performed with respect to the second swimmer.

22. A computerized apparatus having a processor, the processor being adapted to perform the steps of:
obtaining a visual input from one or more cameras observing a water area;
analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources; and wherein said analyzing comprises identifying a spotter observing the second swimmer, wherein said determining the risk level of the second swimmer is based on the spotter observing the second swimmer.

23. A computerized apparatus having a processor, the processor being adapted to perform the steps of:
obtaining a visual input from one or more cameras observing a water area;
analyzing each swimmer in the water area, based on visual input from the one or more cameras, wherein said analyzing comprises determining a risk level of each swimmer, whereby a first risk level is determined for a first swimmer and a second risk level is determined for a second swimmer, wherein the first risk level is higher than the second risk level;
automatically detecting potential drowning events, for each swimmer, wherein said automatically detecting is performed by utilizing computational resources in a non-uniform manner in respect of the first swimmer and for the second swimmer, by utilizing for the first swimmer a first classifier configured to receive a first set of features and use increased computational resources, and by utilizing for the second swimmer a second classifier configured to receive a second set of features and use reduced computational resources, the first classifier and the second classifier configured to predict a likelihood of a potential drowning event, wherein a Cartesian product of domains of the first set of features comprises a larger number of elements than a Cartesian product of domains of the second set of features, wherein the increased computational resources are higher than the reduced computational resources; and
wherein said analyzing comprises identifying a spotter, determining a field of view of the spotter, and wherein said determining the risk level is performed based on the field of view of the spotter.

* * * * *